US010350822B1

(12) United States Patent
Deng et al.

(10) Patent No.: US 10,350,822 B1
(45) Date of Patent: Jul. 16, 2019

(54) DOSAGE FORMS WITH DESIRED RELEASE PROFILES AND METHODS OF DESIGNING AND MAKING THEREOF

(71) Applicant: Triastek Inc., Nanjing (CN)

(72) Inventors: Feihuang Deng, Nanjing (CN); Xiaoling Li, Dublin, CA (US); Senping Cheng, Nanjing (CN)

(73) Assignee: Triastek Inc., Nanjing (CN)

( * ) Notice: Subject to any disclaimer, the term of this patent is extended or adjusted under 35 U.S.C. 154(b) by 0 days.

(21) Appl. No.: 16/049,713

(22) Filed: Jul. 30, 2018

(51) Int. Cl.

| A61K 9/00 | (2006.01) |
|---|---|
| A61K 9/20 | (2006.01) |
| A61K 9/48 | (2006.01) |
| B33Y 10/00 | (2015.01) |
| B33Y 50/02 | (2015.01) |
| B29C 64/118 | (2017.01) |
| B29C 64/393 | (2017.01) |
| B33Y 70/00 | (2015.01) |

(Continued)

(52) U.S. Cl.
CPC .......... *B29C 64/118* (2017.08); *A61K 9/0053* (2013.01); *A61K 9/2086* (2013.01); *A61K 9/4808* (2013.01); *B29C 64/393* (2017.08); *B33Y 10/00* (2014.12); *B33Y 50/02* (2014.12); *A61K 31/415* (2013.01); *A61K 31/4458* (2013.01); *B29K 2105/0035* (2013.01); *B33Y 70/00* (2014.12); *B33Y 80/00* (2014.12)

(58) Field of Classification Search
None
See application file for complete search history.

(56) References Cited

U.S. PATENT DOCUMENTS 5,204,055 A 4/1993 Sachs et al.
5,260,009 A 4/1993 Watling et al.
(Continued)

FOREIGN PATENT DOCUMENTS

CN 105687153 A 6/2016
CN 105690762 A 6/2016
(Continued)

OTHER PUBLICATIONS

Bisht, R. (Jan.-Mar. 2011). "Chronomodulated Drug Delivery System: A Comprehensive Review on the Recent Advances in a New Sub-Discipline of 'Chronopharmaceutics'," *Asian Journal of Pharmaceutics* 5:1-8.
(Continued)

*Primary Examiner* — Benjamin A Schiffman
(74) *Attorney, Agent, or Firm* — Morrison & Foerester LLP

(57) ABSTRACT

In some aspects, the present disclosure provides dosage forms, such as oral drug dosage forms, configured to provide a desired release profile, the dosage forms comprising a multi-layered structure comprising a plurality of layers of a first erodible material admixed with a compound (e.g., a drug) or a reagent, wherein the first erodible material is embedded in a second material not admixed with the compound (e.g., the drug) or the reagent. In other aspects, the present disclosure provides methods of designing, such as obtaining a thickness and/or surface area of a layer comprising an erodible material admixed with a compound (e.g., a drug) or a reagent, and/or amount of the compound (e.g., the drug) or the reagent admixed in the erodible material, and methods of making, such as three-dimensional printing, dosage forms configured to provide desired release profiles.

29 Claims, 9 Drawing Sheets

(51) Int. Cl.
| | |
|---|---|
| B33Y 80/00 | (2015.01) |
| A61K 31/415 | (2006.01) |
| B29K 105/00 | (2006.01) |
| A61K 31/4458 | (2006.01) |

(56) References Cited

U.S. PATENT DOCUMENTS

| | | | |
|---|---|---|---|
| 5,340,656 | A | 8/1994 | Sachs et al. |
| 5,387,380 | A | 2/1995 | Cima et al. |
| 5,490,962 | A | 2/1996 | Cima et al. |
| 5,503,785 | A | 4/1996 | Crump et al. |
| 5,518,690 | A | 5/1996 | Masahashi et al. |
| 5,633,021 | A | 5/1997 | Brown et al. |
| 5,869,170 | A | 2/1999 | Cima et al. |
| 6,280,771 | B1 | 8/2001 | Monkhouse et al. |
| 6,471,992 | B1 | 10/2002 | Yoo et al. |
| 6,514,518 | B2 | 2/2003 | Monkhouse et al. |
| 6,530,958 | B1 | 3/2003 | Cima et al. |
| 6,986,739 | B2 | 1/2006 | Warren et al. |
| 8,828,411 | B2 | 9/2014 | Yoo et al. |
| 2002/0015728 | A1 | 2/2002 | Payumo et al. |
| 2002/0106412 | A1 | 8/2002 | Rowe et al. |
| 2003/0143268 | A1 | 7/2003 | Pryce et al. |
| 2003/0198677 | A1 | 10/2003 | Lewis et al. |
| 2004/0005360 | A1 | 1/2004 | Wang et al. |
| 2016/0354315 | A1 | 12/2016 | Xialoling |
| 2018/0116911 | A1 | 5/2018 | Xialoling |

FOREIGN PATENT DOCUMENTS

| | | |
|---|---|---|
| CN | 205343831 U | 6/2016 |
| CN | 106491551 A | 3/2017 |
| CN | 107019676 A | 8/2017 |
| CN | 108215153 A | 6/2018 |
| CN | 108215154 A | 6/2018 |
| WO | WO2016075497 A1 | 5/2016 |
| WO | WO-2016/192680 A1 | 12/2016 |
| WO | WO-2017/010938 A1 | 1/2017 |
| WO | WO-2017/193099 A1 | 11/2017 |

OTHER PUBLICATIONS

Ganadhi, B.R. et al. (2011). "Chronopharmaceutics: As a Clinically Relevant Drug Delivery System," *Drug Delivery* 18(1):1-18.

Gibson, I. et al. (2015). "Additive Manufacturing Technologies: 3D Printing, Rapid Prototyping, and Direct Digital Manufacturing," 2nd ed. *Johnson Matthey Techno. Rev.* 59(3):193-198.

Goole, J. et al. (2016, e-pub. Jan. 3, 2016). "3D Printing in Pharmaceutics: A New Tool for Designing Customized Drug Delivery Systems," *Int. J. Pharm.* 499:376-394.

Goyanes, A. et al. (2015). "3D Printing of Medicines: Engineering Novel Oral Devices with Unique Design and Drug Release Characteristics," *Molecular Pharmaceutics* 12(11):4077-4084, 8 pages.

"Guidance for Industry: Dissolution Testing of Immediate Release Solid Oral Dosage Forms," (Aug. 1997). *CDER*, 17 pages.

Katstra, W.E. et al. (May 3, 2000). "Oral Dosage Forms Fabricated by Three Dimensional Printing," *J. Control. Release* 66(1):1-9.

Katstra, W.E. (Jun. 2001). "Fabrication of Complex Oral Delivery Forms by Three Dimensional Printing™," *Dissertation in Materials Science and Engineering, Massachusetts Institute of Technology*, 243 pages.

Khaled, S.A. et al. (2015, e-pub. Sep. 25, 2015). "3D Printing of Five-In-One Dose Combination Polypill With Defined Immediate and Sustained Release Profiles," *J. of Controlled Release* 217:308-314.

Melchels, F.P.W. et al. (Aug. 2010, e-pub. May 15, 2010). "A Review on Stereolithography and Its Application in Biomedical Engineering," *Biomaterials* 31(24):6121-6130.

Poh, P.S.P. et al. (Dec. 15, 2016, e-pub. Aug. 1, 2016). "Polylactides in Additive Biomanufacturing," *Advanced Drug Delivery Reviews* 107:228-246.

Sun, Y. et al. (2015). "Printing Tablets with Fully Customizable Release Profiles for Personalized Medicine," *Adv. Mater.* 27:7847-7853.

U.S. Appl. No. 15/937,528, Li et al., filed Mar. 27, 2018.
U.S. Appl. No. 16/028,305, Li et al., filed Jul. 5, 2018.
International Search Report and Written Opinion, dated Mar. 25. 2019, for PCT/CN2018/123399, filed Dec. 25, 2018, 8 pages.

DOSAGE FORMS WITH DESIRED RELEASE PROFILES AND METHODS OF DESIGNING AND MAKING THEREOF

CROSS-REFERENCE TO RELATED APPLICATIONS

This application claims priority benefit under 35 U.S.C. § 365(a) of International PCT Application No. PCT/CN2018/071967, filed on Jan. 9, 2018, entitled "DOSAGE FORMS WITH DESIRED RELEASE PROFILES AND METHODS OF DESIGNING AND MAKING THEREOF," the entire contents of which are incorporated herein by reference for all purposes.

TECHNICAL FIELD

In some aspects, the present disclosure provides dosage forms, such as drug dosage forms, configured to provide a desired release profile, the dosage forms comprising a multi-layered structure comprising a plurality of layers of a first erodible material admixed with a drug or a reagent, wherein the first erodible material is embedded in a second material not admixed with the compound (e.g., the drug) or the reagent. In other aspects, the present disclosure provides methods of designing and methods of making, such as three-dimensional printing, dosage forms configured to provide desired release profiles.

BACKGROUND

The growing understanding of the mechanisms of drugs and reagents involved with use, efficacy, and toxicity illustrates the importance of precision delivery both in location and timing. To achieve improved use, efficacy, and safety, certain drugs and reagents, such as drug combinations, may require complex administration schemes or release profiles to control release of one or more drug or reagent components to achieve a desired absorption, distribution, metabolism, and elimination profile. However, the demands required to achieve consistent precision delivery often run counter to ensuring proper use and patient compliance via simplicity of administration, e.g., a once-daily pill.

Three-dimensional (3D) printing enables precise placement of materials on a substrate to form three-dimensional structures from computer-generated designs. For example, in an application of 3D printing for producing drug dosage forms, a negative mold was 3D printed and subsequently used to form a shape of an erodible material admixed with a drug by pouring the erodible material admixed with the drug into the negative mold (WO2017010938). The molded erodible material admixed with a drug was then manually assembled into the final drug dosage form. However, such techniques are limited, e.g., limited throughput, need for extra manufacturing steps required when using a mold process, and limited drug dosage form design capability/flexibility due to the molding process.

All references cited herein, including patent applications and publications, are incorporated by reference in their entirety.

BRIEF SUMMARY

The present disclosure provides, e.g., dosage forms configured and formulated to provide a desired release profile, and methods of designing and methods of making thereof. Although much of the application discusses drug dosage forms, such as oral drug dosage forms, one of ordinary skill in the art will readily understand that this disclosure also pertains to and teaches other dosage forms configured and formulated to provide a desired release profile of, e.g., a compound, such an implant drug dosage form or a dosage form comprising a reagent (reagent dosage form) configured and formulated to provide a desired reagent release profile.

In one aspect, the present disclosure provides methods for three-dimensional printing of a dosage form, such as a drug dosage form (for example oral drug dosage form), formulated and configured to provide a desired release profile, such as a desired drug release profile, comprising: dispensing a first erodible material admixed with a compound (e.g., a drug) and a second material not admixed with the compound (e.g., the drug) to produce a multi-layered structure comprising a plurality of layers of the first erodible material, wherein the first erodible material is embedded in the second material, wherein each layer of the first erodible material has a pre-determined surface area, thickness, and mass fraction, such as a drug mass fraction, wherein the pre-determined surface area, thickness, and/or drug mass fraction correlate with the desired release profile, and wherein upon exposure to a bodily fluid, such as a gastrointestinal fluid, the compound (e.g., drug) is released in accordance with the desired release profile.

In some embodiments, the methods further comprise providing the desired release profile, such as the desired rug release profile, prior to the dispensing step.

In some embodiments, the methods further comprise creating a virtual image of the dosage form prior to the dispensing step.

In some embodiments, the methods further comprise creating a computer model that contains the pre-determined parameters prior to the dispensing step.

In some embodiments, the methods further comprise feeding the pre-determined parameters to the three-dimensional printer prior to the dispensing step.

In some embodiments, the first erodible material admixed with the compound (e.g., the drug) and the second material not admixed with the compound (e.g., the drug) are dispensed separately.

In some embodiments, the first erodible material admixed with the compound (e.g., the drug) and the second material not admixed with the compound (e.g., the drug) are dispensed sequentially.

In some embodiments, the surface areas of the first erodible material in at least two of the layers are different from each other.

In some embodiments, the thicknesses of each of the plurality of layers of the first erodible material are the same.

In some embodiments, the thickness of at least two of the layers of the first erodible materials are different from each other.

In some embodiments, the mass fraction, such as the drug mass fraction, in each of the plurality of layers of the first erodible material are the same.

In some embodiments, the mass fractions, such as drug mass fractions, in at least two of the layers of the first erodible materials are different from each other.

In some embodiments, the second material is a second erodible material.

In some embodiments, the first erodible material and the second erodible material are different from each other. In some embodiments, the first erodible material and the second erodible material are the same.

In some embodiments, the second material is an insulating material that is impermeable to the bodily fluid, such as gastrointestinal fluid, wherein the insulating material forms a barrier between the bodily fluid and at least a portion of the multi-layered structure. In some embodiments, the methods further comprise dispensing an insulating material that is impermeable to the bodily fluid, such as gastrointestinal fluid, wherein the insulating material forms a barrier between the bodily fluid and at least a portion of the multi-layered structure.

In some embodiments, the first erodible material and the second material are dispensed by different printing heads. In some embodiments, the first erodible material, the second material, and the insulating material are dispensed by different printing heads.

In some embodiments, the three-dimensional printing is carried out by fused deposition modeling (FDM). In some embodiments, the FDM is a non-filament FDM. In some embodiments, the FDM is a filament FDM. In some embodiments, the three-dimensional printing is carried out by hot melt extrusion coupled with a three-dimensional printing technique, such as FDM.

In some embodiments, the first erodible material and the second material have the same erosion rate.

In some embodiments, the thickness of each layer is no more than about 0.2 mm.

In some embodiments, the methods further comprise dispensing an intermediate material not admixed with the drug, wherein the intermediate material forms an intermediate layer between two or more layers of the first erodible material. In some embodiments, the intermediate material is the same as the first erodible material or the second material.

In some embodiments, the methods further comprise dispensing an intermediate material not admixed with the drug, wherein the intermediate material forms an intermediate layer between two or more layers of the first erodible material. In some embodiments, the intermediate material is the same as the first erodible material.

In some embodiments, the compound (e.g., drug) is to be released at an increasing rate. In some embodiments, the compound (e.g., drug) is to be released at a decreasing rate. In some embodiments, the compound (e.g., drug) is to be released at an increasing rate followed by a decreasing rate, or vice versa. In some embodiments, the compound (e.g., drug) is to be released in an oscillating pattern, such as an alternating pattern.

In some embodiments, the dosage form, such as a drug dosage form, further comprises a, e.g., second drug. In some embodiments, e.g., the second drug is admixed with the first erodible material.

In some embodiments, the methods further comprise dispensing a third erodible material admixed with a, e.g., second drug, wherein the multi-layered structure further comprises a plurality of layers of the third erodible material, wherein the third material is embedded in the second material. In some embodiments, each layer of the third erodible material has a pre-determined surface area, thickness, and mass fraction, such as drug mass fraction, wherein the pre-determined surface area, thickness, and/or mass fraction correlate with a second desired release profile, and wherein upon exposure to the bodily fluid, such as gastrointestinal fluid, the, e.g., second drug is released in accordance with the second desired release profile. In some embodiments, the third erodible material is the same as the first erodible material.

In some embodiments, the erosion of the first erodible material is pH dependent. In some embodiments, the erosion of the third erodible material is pH dependent.

In some embodiments, the drug dosage form is an oral drug dosage form. In some embodiments, the bodily fluid is gastrointestinal fluid.

In another aspect, the present disclosure provides methods of designing a dosage form, such as a drug dosage form, to provide a desired release profile, such as a desired drug release profile, wherein the dosage form comprises a multi-layered structure comprising a plurality of layers of a first erodible material admixed with a compound (e.g., a drug), wherein the first erodible material is embedded in a second material not admixed with the compound (e.g., the drug), the methods comprising: (a) selecting the first erodible material and the second material for forming the multi-layered structure; (b) obtaining an erosion rate of first erodible material; and (c) determining the thickness, surface area, and/or mass fraction, such as drug mass fraction, in each layer based on the release rate of the compound (e.g., the drug) and the desired release profile.

In some embodiments, the methods further comprise obtaining the desired release profile, such as the desired drug release profile.

In some embodiments, the methods further comprise dispensing the first erodible material admixed with the compound (e.g., the drug) and the second material not admixed with the compound (e.g., the drug) based on the determined thickness, surface area, and/or mass fraction, such as drug mass fraction.

In some embodiments, the methods further comprise obtaining a desired release profile, such as a desire drug release profile.

In some embodiments, the multi-layered structure further comprises a plurality of second layers of a third erodible material admixed with a, e.g., second drug, and wherein the method further comprises: determining the release rate of the, e.g., second drug from the third erodible material; and determining the thickness, surface area, and/or mass fraction, such as drug mass fraction, in each second layer based on the release rate of the, e.g., second drug and the desired release profile.

In some embodiments, the methods further comprise dispensing the third erodible material admixed with the, e.g., second drug based on the determined thickness, surface area, and/or mass fraction, such as drug mass fraction.

In one aspect, the present disclosure provides methods for three-dimensional ("3D") printing of a dosage form, such as a drug dosage form, formulated and configured to provide a desired release profile, such as a desired drug release profile, wherein the dosage form comprises a multi-layered structure comprising a plurality of layers of a first erodible material admixed with a compound (e.g., a drug), wherein the first erodible material is embedded in a second material not admixed with the compound (e.g., the drug), the method comprising: (a) determining the thickness, surface area, and/or mass fraction, such as drug mass fraction, in each layer based on the release rate of the compound (e.g., the drug) and the desired release profile; and (b) dispensing the first erodible material admixed with the compound (e.g., the drug) and the second material not admixed with the compound (e.g., the drug) based on the determined thickness, surface area, and/or mass fraction, such as drug mass fraction.

In some embodiments, the thickness (H) of the layer of the first erodible material is determined based on the erosion rate of the first erodible material admixed with the drug ($v_E$) and the time interval between two different datapoints on the drug release profile ($t_E$), wherein $$H = t_E * v_E.$$

In some embodiments, the mass fraction ($m_F$), such as drug mass fraction, in the first erodible material is determined based on the percentage, in decimal form, of the total compound (e.g., drug) in the dosage form that is in the layer of the erodible material admixed with the compound (e.g., drug) (% L), the total mass of the compound (e.g., the drug) in the drug dosage form ($m_{DTot}$), the density of the erodible material admixed with the compound (e.g., the drug) ($\rho$), and the volume ($V_{vol}$) of the layer of the erodible material, wherein $$m_F = \frac{\%_L * m_{DTot}}{\rho * V_{vol}}.$$

In some embodiments, the total surface area ($S_t$) of the layers of the first erodible material that are exposed to the bodily fluid, such as gastrointestinal fluid, at the same time is determined by the mass fraction ($m_F$), such as drug mass fraction, and the thickness of the layers of first erodible material, wherein $$S_t = \frac{\%_L * m_{DTot}}{\rho * H * m_F}.$$

In some embodiments, the methods further comprise: (i) determining the release profile, such as the drug release profile, of the produced dosage form; (ii) comparing the release profile of the dosage form with the desired release profile; and (iii) adjusting the design of the dosage form by altering one or more of: the first erodible material, the second material, the surface area of the one or more of the layers of the first erodible material, the thickness of one or more layers of the first erodible material, and the mass fraction of the compound (e.g., the drug) in one or more layers of the first erodible material.

In some embodiments, there is provided a method for three-dimensional ("3D") printing of an oral drug dosage form formulated and configured to provide a desired drug release profile, wherein the drug dosage form comprises a multi-layered structure comprising a plurality of layers of a first erodible material admixed with a drug having a pre-determined drug mass faction ($m_F$), wherein the first erodible material is embedded in a second material not admixed with the drug, the method comprising: (a) dividing the desired drug release profile into a plurality of time intervals ($t_n$), each time interval corresponding to a layer in the multi-layered structure; (b) calculating the percentage of drugs to be released during each time interval (%$_L$); (c) calculating the thickness of each layer ($H_n$) of the multi-layered structure based on the erosion rate of the first erodible material (V), wherein $H_n = t_n * V$; (d) calculating the surface area of each layer based on %$_L$, $H_n$, $m_F$, total amount of drug in the oral drug dosage form ($m_{DTot}$), and the density of the first erodible material ($\rho$), wherein:

$$S_n = \frac{\%_L * m_{DTot}}{\rho * Hn * m_F}$$

(e) dispensing the first erodible material admixed with the drug based on the determined $H_n$ and $S_n$ for each layer, thereby printing the multi-layered structure; and (f) before, after, or during step (e), dispensing the second material not admixed with the drug.

In some embodiments, the 3D printing method further comprises dispensing a top erodible material not admixed with the drug on top of the multi-layered structure to form a top layer, wherein the surface area of the top layer is the same or larger than the first layer of the multi-layered structure immediately underneath the top layer. In some embodiments, the thickness of the top layer is determined based on the delay time needed for the drug release from the multi-layered structure. In some embodiments, the top erodible material is the same as the first erodible material. In some embodiments, the top erodible material is different from the first erodible material.

In some embodiments according any one of the 3D printing methods described above, the second material is erodible, and can have the same or a different erosion rate as that of the first erodible material. In other embodiments, the second material is an insulating material that is impermeable to bodily fluid, wherein the insulating material forms a barrier between the bodily fluid and at least a portion of the multi-layered structure.

In some embodiments according to any one of the 3D printing methods described above, further comprising dispensing an insulating material that is impermeable to bodily fluid, wherein the insulating material forms a barrier between the bodily fluid and at least a portion of the multi-layered structure.

In some embodiments according to any one of the 3D printing methods described above, further comprising dispensing an intermediate material not admixed with the drug, wherein the intermediate material forms one or more intermediate layers between two or more layers of the first erodible material. In some embodiments, the intermediate material is the same as the first erodible material. In some embodiments, the intermediate layer is different from the first erodible material.

In some embodiments according to any of the 3D printing methods described above, wherein the three-dimensional printing is carried out by fused deposition modeling (FDM), such as non-filament FDM. In some embodiments, the first erodible material and the second material are printed by different printing heads. In some embodiments, the first erodible material and the top erodible material are printed by different printing heads. In some embodiments, the first erodible material, the second erodible material (if any), and the insulating material are printed by a different printing heads.

The method of any one of the 3D printing methods described above, further comprising: i) determining the drug release profile of the oral drug dosage form produced by the method of any one of the 3D printing methods described above; ii) comparing the drug release profile of the oral drug dosage form with the desired drug release profile; iii) adjusting one or more parameters selected from: the first erodible material, the second material, the surface area of the one or more of the layers of the first erodible material, the thickness of one or more layers of the first erodible material, and the mass fraction of the drug in one or more layers of the first erodible material; and iv) three-dimensional printing of a second oral drug dosage form based on the adjusted parameters.

In some embodiments according any one of the 3D printing method described above, wherein the release profile of the oral drug dosage form or second drug oral dosage form is equivalent to the desired release profile based on Chow's method or similarity factor calculation method.

In some embodiments according to any one of the 3D printing method described above, the method further comprises creating a virtual image of the drug dosage form prior to the dispending steps, creating a computer model that contains the pre-determined parameters prior to the dispensing step, and/or feeding the pre-determined parameters to the three-dimensional printer prior to the dispensing step.

In some embodiments according to any one of the 3D printing method described above, the surface area of each of the plurality of the layers of the first erodible material in the multi-layered structure decreases sequentially from the surface to the interior of the oral dosage form, wherein when the oral dosage form is exposed to a bodily fluid the plurality of layers are exposed to the bodily fluid in a sequential pattern, with the layer with the largest surface area exposed to the bodily fluid first.

In some embodiments according to any one of the 3D printing method described above, the oral drug dosage form comprises two or more multi-layered structures.

In some embodiments, there is provided a method for three-dimensional ("3D") printing of an oral drug dosage form formulated and configured to provide a first desired drug release profile and a second desired drug release profile, wherein the drug dosage form comprises a first multi-layered structure comprising a plurality of layers of a first erodible material admixed with a drug having a pre-determined drug mass faction ($m_F$), wherein the first erodible material is embedded in a second material not admixed with a first drug, and a second multi-layered structure comprising a plurality of layers of a third erodible material admixed with a second drug having a pre-determined drug mass faction, wherein the third erodible material is embedded in a fourth material not admixed with the drug, the method comprising: (a) dividing each of the desired drug release profile into a plurality of time intervals ($t_n$), each time interval corresponding to a layer in a corresponding multi-layered structure; (b) calculating the percentage of drugs to be released during each time interval ($\%_L$); (c) calculating the thickness of each layer ($H_n$) of the multi-layered structures based on the erosion rate of the first erodible material or third erodible material (V), wherein $H_n = t_n * V$; (d) calculating the surface area of each layer based on $\%_L$, $H_n$, $m_F$, total amount of drug in the oral drug dosage form ($m_{DTot}$), and the density of the first or first erodible material ($\rho$), wherein:

$$S_n = \frac{\%_L * m_{DTot}}{\rho * Hn * m_F}$$

(e) dispensing the first erodible material admixed with the first drug and third erodible material admixed with the second drug based on the determined $H_n$ and $S_n$ for each layer, thereby printing the two multi-layered structures; and (f) before, after, or during step (e), dispensing the second material and fourth material not admixed with the drug. In some embodiments, the first erodible material and the third erodible material are the same. In some embodiments, the second and fourth materials are the same. In some embodiments, the first drug and the second drug are the same. In some embodiments, the first drug and the second drug are different.

In another aspect, the present disclosure provides dosage forms, such as oral dosage forms, produced according to any one of the methods described herein. In some embodiments, the dosage form, such as drug dosage form, further comprises an enteric coating.

These and other aspects and advantages of the present disclosure will become apparent from the subsequent detailed description and the appended claims. It is to be understood that one, some, or all of the properties of the various embodiments described herein may be combined to form other embodiments of the present disclosure.

BRIEF DESCRIPTION OF THE DRAWINGS

FIG. 2A shows a cross-sectional view of the exemplary dosage form 200. FIG. 2B and FIG. 2C show external views of exemplary drug dosage forms 240, 265 having the cross-section illustrated in FIG. 2A.

FIG. 3A shows an external view of the exemplary drug dosage form 300 with translucently illustrated components to illustrate internal features of the drug dosage form. FIG. 3B shows a cross-sectional view of the exemplary drug dosage form 300.

FIG. 4A shows a cross-sectional view of the exemplary dosage form 400. FIG. 4B shows a cross-sectional view of the exemplary dosage form 425. FIG. 4C shows an external view of the exemplary drug dosage form 425 having the cross-section illustrated in FIG. 4B.

FIG. 8A shows an external view of the exemplary drug dosage form 800 with translucently illustrated components to illustrate internal features of the drug dosage form. FIG. 8B shows a cross-sectional view of the exemplary dosage form 800.

FIG. 9A shows an external view of the exemplary drug dosage form 900 with translucently illustrated components to illustrate internal features of the drug dosage form. FIG. 9B shows a cross-sectional view of the exemplary dosage form 900.

DETAILED DESCRIPTION

Figure 1:
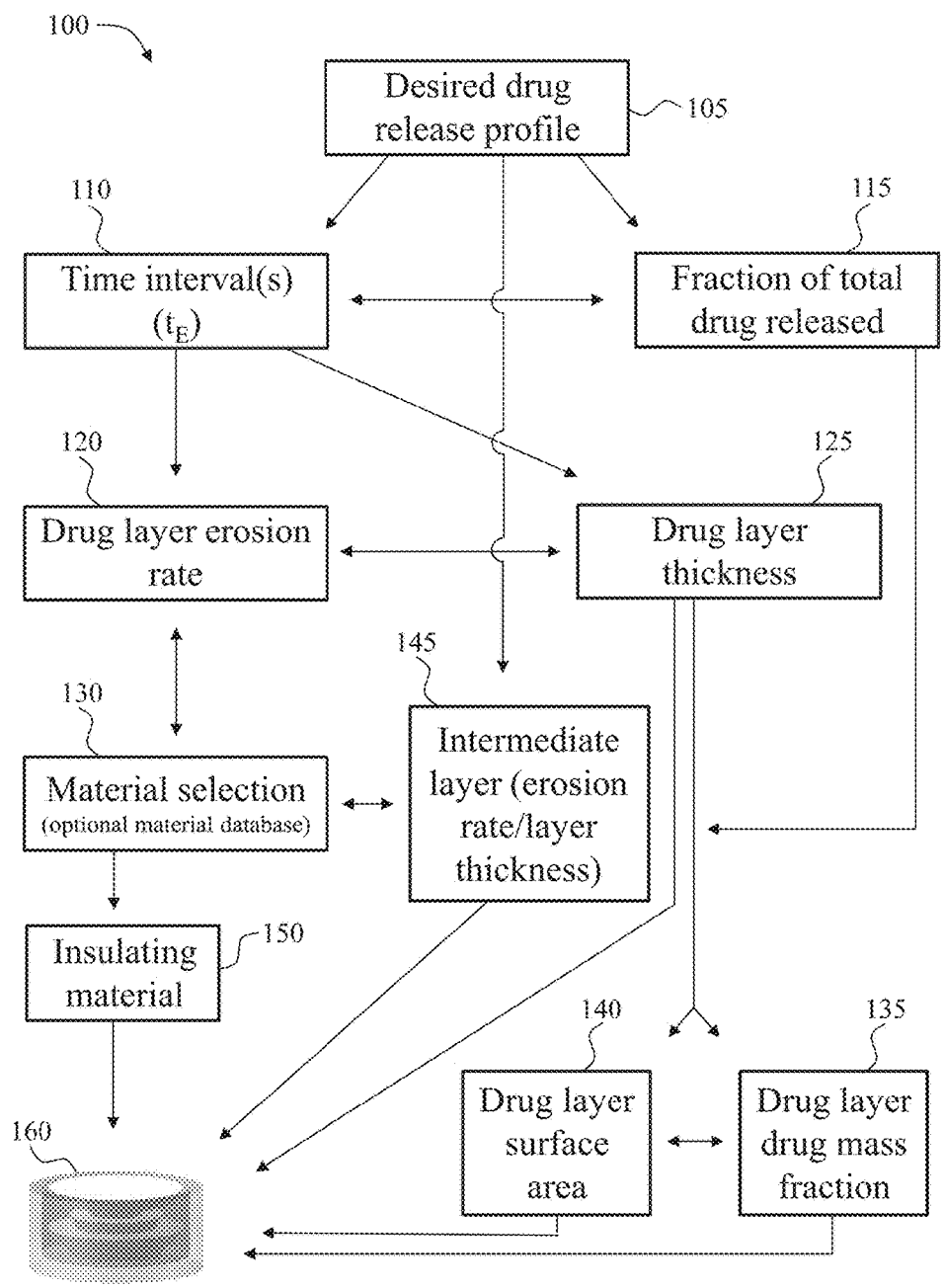
FIG. 1 shows an exemplary schematic 100 for designing a drug dosage form 160 formulated and configured to provide a desired drug release profile 105.

The present application provides methods of making, e.g., three-dimensional printing of drug dosage forms comprising a multi-layered structure comprising a plurality of layers of a first erodible material admixed with a drug, wherein the erosion of the first erodible material admixed with the drug correlates with release rate of the drug from the drug dosage form. Using the methods disclosed herein, drug dosage forms, such as oral drug dosage forms or implant drug dosage forms, may provide any desired drug release profile based on controlling various parameters, e.g., thickness of a layer of a first erodible material admixed with a drug, surface area of the layer of the first erodible material, and drug mass fraction of the layer of the first erodible material. Drug dosage forms with a desired drug release profile of a drug, or multiple drugs, may be readily designed and printed using three-dimensional printing techniques. Such drug dosage forms may be designed to, e.g., improve treatment efficacy, reduce toxicity, and increase patient compliance.

Methods of calibrating, such as adjusting, the dosage forms based on a dissolution profile, such as an in vitro dissolution profile, to improve similarity of an experimentally determined release profile with a desired release profile are also provided herein.

Although much of the application discusses drug dosage forms, such as oral drug dosage forms or implant drug dosage forms, one of ordinary skill in the art will readily understand that this disclosure also applies and pertains to other dosage forms configured and formulated to provide a desired release profile of any compound, such as a dosage form comprising a reagent (i.e., reagent dosage form) configured and formulated to provide a desired reagent release profile. Thus, the present disclosure provides, in some aspects, dosage forms, such as drug dosage forms or reagent dosage forms, configured to provide a desired release profile of a compound (e.g., a drug) or reagent, as well as methods of designing and methods of 3D printing thereof, wherein the dosage forms comprise a multi-layered structure comprising a plurality of layers of a first erodible material admixed with the compound (e.g., the drug) or reagent, wherein the first erodible material is embedded in a second material not admixed with the compound (e.g., the drug) or reagent.

Definitions

The term "comprises" and grammatical equivalents thereof are used herein to mean that other components, ingredients, steps, etc. are optionally present. For example, an article "comprising" components A, B, and C can consist of (i.e., contain only) components A, B, and C, or can contain not only components A, B, and C but also one or more other components. It is understood that "comprises" and grammatical equivalents thereof include "consisting of" or "consisting essentially of."

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein and in the appended claims, the singular forms "a," "or," and "the" include plural referents unless the context clearly dictates otherwise.

As used herein, the term "individual" refers to a mammal and includes, but is not limited to, human, bovine, horse, feline, canine, rodent, or primate. In some embodiments, the individual is human.

The term "layer" described herein in the context of a multi-layered structure refers to one of the plurality of layers in the multi-layer structure, the thickness of which is determined or pre-determined during the design of the dosage forms. The thickness of a layer in a multi-layered structure may or may not have the same thickness as that of the unit deposition layer during a layer-by-layer 3D printing process.

In the embodiments herein, use of a specific mathematical equation is not intended to limit the determination of a characteristic of the drug dosage form, or materials thereof, and it is recognized that there are other means, e.g., mathematical equations, or variables for obtaining characteristics of drug dosage forms, or materials thereof, useful for designing a drug dosage form with a desired release profile.

Methods of Designing a Dosage Form

The present disclosure provides methods of designing a dosage form, such as an oral drug dosage form, an implant dosage form, or a reagent dosage form, to provide a desired release profile of a compound (e.g., a drug), wherein the dosage form comprises a multi-layered structure comprising a plurality of layers of a first erodible material admixed with the compound (e.g., the drug), wherein the first erodible material is embedded in a second material not admixed with the compound (e.g., the drug).

As illustrated in the schematic 100 of FIG. 1, there are multiple steps and routes for designing a dosage form, such as an oral drug dosage form, to provide a desired release profile. The methods disclosed herein may be guided by possible design restrictions, e.g., pre-selection of a material such as a first erodible material admixed with a drug 130 or pre-selection of thickness of a layer of a first erodible material admixed with a drug 125 (FIG. 1). In view of the disclosure herein, one of ordinary skill in the art will understand the relationships between the steps and, under a set of circumstances, a method or methods of designing a drug dosage form to provide a desired drug release profile of a drug.

In some embodiments, the method of designing a dosage form, such as an oral drug dosage form, to provide a desired release profile, wherein the dosage form comprises a multi-layered structure comprising a plurality of layers of a first erodible material admixed with a compound (e.g., a drug), and wherein the first erodible material is embedded in a second material not admixed with the drug, comprises: (a) selecting the first erodible material and the second material for forming the multi-layered structure; (b) obtaining an erosion rate of first erodible material; and (c) determining the thickness, surface area, and/or mass fraction, such as drug mass fraction, in each layer based on the release rate of the compound (e.g., the drug) and the desired release profile. In some embodiments, the multi-layered structure further comprises a plurality of second layers of a third erodible material admixed with a, e.g., second drug, wherein the method further comprises: determining the drug release rate of the second drug from the third erodible material; and determining the thickness, surface area, and/or drug mass fraction in each second layer based on the release rate of the second drug and the desired drug release profile.

As shown in FIG. 1, in some embodiments, the method of designing a drug dosage form to provide a desired drug release profile of a drug comprises obtaining, e.g., selecting, a desired drug release profile of the drug 105. In some embodiments, the method comprises dividing the desired drug release profile into time intervals 110 (e.g., based on the number of layers of a first erodible material admixed with the drug intended for the drug dosage form) and then determining the fraction of total drug released 115 during said time interval. In some embodiments, the method comprises determining an erosion rate of the first erodible material admixed with the drug 120 and the thickness of the layer of the first erodible admixed with the drug 125 using said time interval and the selected material for the first erodible material admixed with the drug 130. In some embodiments, the method comprises determining a surface area of the layer of first erodible material admixed with the drug 140 and the drug mass fraction of the layer of the first erodible material admixed with the drug 135 using the fraction of total drug released during said time interval and the thickness of the layer of the first erodible material admixed with the drug. In some embodiments, the method further comprises determining the thickness and surface area of an intermediate layer 145. In some embodiments, the method further comprises selecting an insulating material 150.

Figure 2A:
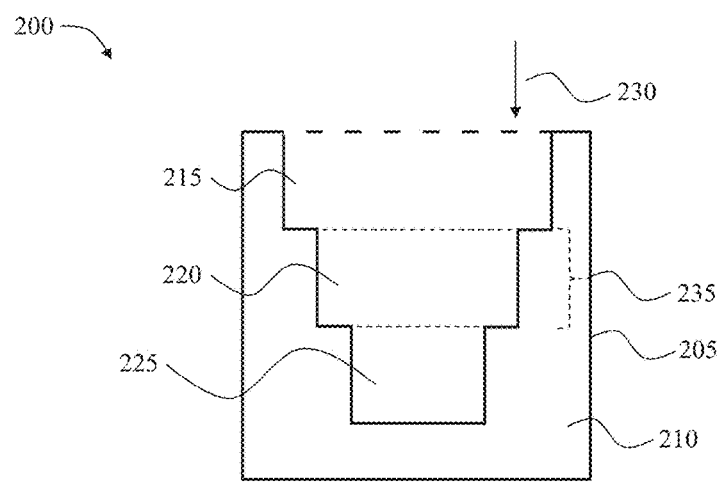
FIGS. 2A-2C show exemplary drug dosage forms 200, 240, 265 formulated and configured to provide a desired drug release profile.

In some embodiments, the methods described herein may be useful for designing a drug dosage form comprising a multi-layered structure comprising a plurality of layers of a first erodible material admixed with a drug, wherein the first erodible material is embedded in a second material, wherein the plurality of layers comprises a first layer and a second layer, wherein the first layer will be exposed to a bodily fluid prior to the second layer, and wherein the surface area of the first layer is larger than the second layer (e.g., FIG. 2A). In some embodiments, the second layer is positioned so that once the first layer has eroded, the complete surface area of the second layer will be exposed to the bodily fluid (e.g., FIG. 2A, 220). In some embodiments, the drug dosage form may comprise two or more plurality of layers of a first erodible material admixed with a drug, wherein each of the plurality of layers comprises a first layer and a second layer, wherein the first layer will be exposed to a bodily fluid prior to the second layer, and wherein the surface area of the first layer is larger than the second layer (e.g., FIG. 4A).

In some embodiments, the methods of designing a drug dosage form described herein may be performed, in whole or in part, on a computer system. In some embodiments, the computer system comprises a user interface. In some embodiments, the method comprises inputting one or more parameters of the drug dosage form into the computer system. In some embodiments, the computer system is used to calculate the parameters of the drug dosage form to provide a desired drug release profile. In some embodiments, the computer system comprises three-dimensional drawing software. In some embodiments, the computer system is used to create a three-dimensional drawing of a drug dosage form based on the pre-determined parameters of the drug dosage form. In some embodiments, the computer system comprises slicing software. In some embodiments, the computer system is used to convert a three-dimensional drawing of a drug dosage form into three-dimensional printing code, e.g., G code. In some embodiments, the computer system executes the three-dimensional printing code, thereby printing a drug dosage form.

A. Desired Release Profile

The methods disclosed herein of designing a dosage form, such as an oral drug dosage form, to provide a desired release profile of a compound (e.g., a drug) may be used to design the dosage form with any desired release profile. In some embodiments, the desired drug release profile comprises the fraction or percentage of total (i.e., cumulative) drug to be released from the drug dosage form by time points following administration or subsequent commencement of drug release from the drug dosage form (e.g., for enteric-coated oral drug dosage forms). In some embodiments, the desired drug release profile comprises the actual amount or concentration of a drug to be released from a release medium.

In some embodiments, the method of designing a drug dosage form to provide a desired drug release profile, wherein the drug dosage form comprises a multi-layered structure comprising a plurality of layers of a first erodible material admixed with a drug, wherein the first erodible material is embedded in a second material not admixed with the drug, comprises obtaining or selecting the desired drug release profile of the drug dosage form. In some embodiments, the desired drug release profile is pre-determined.

In some embodiments, the drug dosage form comprises two or more drugs, such as about any of 5 or more, 10 or more, 20 or more, 30 or more, or 50 or more, wherein each drug has a desired drug release profile. In some embodiments, the drug dosage form comprises two or more drugs, wherein at least two drugs have a different desired drug release profile.

In some embodiments, the drug will start to be released from a drug dosage form once a layer of a first erodible material comprising the drug is exposed to a solution, such as bodily fluid, e.g., gastrointestinal (GI) fluid. In some embodiments, the desired drug release profile of a drug dosage form is for the period of time from oral administration to complete release of a drug contained in the drug dosage form. In some embodiments, the desired drug release profile comprises an initial delay period prior to a desired drug release period, wherein the initial delay period is a patient-specific period of time or an estimated period of time, e.g., due to use of an enteric-coated oral dosage form.

In some embodiments, the desired drug release profile of a drug dosage form comprises a zero-order release profile, a first-order release profile, a delayed release profile, a pulsed release profile, an iterative pulsed release profile, an immediate release profile, a sustained release profile, or a combination thereof.

In some embodiments, the total time of a desired release profile of a dosage form is about 1 hour to about 12 months. In some embodiments, the total time of a desired release profile of a dosage form is greater than about any of 1 hour, 6 hours, 12 hours, 24 hours, 2 days, 3 days, 4 days, 5 days, 6 days, 7 days, 8 days, 9 days, 10 days, 11 days, 12 days, 20 days, 1 month, 2 months, 3 months, 4 months, 5 months, 6 months, 7 months, 8 months, 9 months, 10 months, 11 months, or 12 months. In some embodiments, the total time of a desired release profile of a dosage form is about any of 1 hour, 6 hours, 12 hours, 24 hours, 2 days, 3 days, 4 days, 5 days, 6 days, 7 days, 8 days, 9 days, 10 days, 11 days, 12 days, 20 days, 1 month, 2 months, 3 months, 4 months, 5 months, 6 months, 7 months, 8 months, 9 months, 10 months, 11 months, or 12 months.

In some embodiments, the total time of a desired drug release profile of a drug dosage form is about 1 hour to about 72 hours, such as any of about 1 hour to about 6 hours, about 1 hour to about 12 hours, about 1 hour to about 18 hours, about 1 hour to about 24 hours, about 1 hour to about 30 hours, about 1 hour to about 36 hours, about 1 hour to about 42 hours, about 1 hour to about 48 hours, about 1 hour to about 54 hours, about 1 hour to about 60 hours, or about 1 hour to about 66 hours. In some embodiments, the total time of a desired drug release profile of a drug dosage form is about any of 1 hour, 2 hours, 3 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours. In some embodiments, the total time of a desired drug release profile of a drug dosage form is greater than or about 6 hours, greater than or about 12 hours, greater than or about 18 hours, greater than or about 24 hours, greater than or about 30 hours, greater than or about 36 hours, greater than or about 42 hours, greater than or about 48 hours, greater than or about 54 hours, greater than or about 60 hours, greater than or about 66 hours, or greater than or about 72 hours. In some embodiments, the total time of a desired drug release profile of a drug dosage form is less than or about 6 hours, less than or about 12 hours, less than or about 18 hours, less than or about 24 hours, less than or about 30 hours, less than or about 36 hours, less than or about 42 hours, less than or about 48 hours, less than or about 54 hours, less than or about 60 hours, less than or about 66 hours, or less than or about 72 hours.

As shown in the schematic 100 of FIG. 1, a desired drug release profile 105 may provide information regarding one or more time intervals ($t_E$) of the desired drug release profile 110 and a fraction or percentage of total drug released over each time interval 115.

In some embodiments, the method of designing a drug dosage form to provide a desired drug release profile of a drug comprises: obtaining or selecting one or more time points forming one or more time intervals over at least a portion of time of the desired drug release profile; and subsequently obtaining the corresponding fraction of the total drug released from the drug dosage form during each time interval.

The time points used in the methods disclosed herein may be of any suitable size, e.g., seconds, minutes, and/or hours. In some embodiments, the one or more time points over the time of the desired drug release profile are based on a uniform time intervals (e.g., at 1, 2, and 3 hours post-administration or commencement of drug release), a non-uniform time interval (e.g., at 1, 2, 4, and 8 hours post-administration or commencement of drug release), or a combination thereof. In some embodiments, the time points over the time of the desired drug release profile are at about any of 5 minutes, 10 minutes, 15 minutes, 20 minutes, 30 minutes, 45 minutes, 60 minutes, 90 minutes, 120 minutes, 180 minutes, 240 minutes, 300 minutes, or 360 minutes. In some embodiments, the time points over the time of the desired drug release profile are at about any of 15 minutes, 30 minutes, 45 minutes, 60 minutes, 90 minutes, 2 hours, 3 hours, 4 hours, 5 hours, 6 hours, 8 hours, 10 hours, 12 hours, or 24 hours.

In some embodiments, the number of time points, and thus time intervals, is based on the number of layers of a first erodible material admixed with a drug in a drug dosage form. In some embodiments, the number of time points or time intervals is between about 1 to about 100, such as between any of about 1 to about 5, about 5 to about 10, about 10 to about 15, about 5 to about 20, about 10 to about 20, about 15 to about 20, about 5 to about 50, or about 10 to about 100. In some embodiments, the number of time points or time intervals is about any of 1, 2, 3, 4, 5, 6, 7, 8, 9, 10, 11, 12, 13, 14, 15, 16, 17, 18, 19, 20, 25, 30, 35, 40, 45, 50, 75, or 100.

In some embodiments, the method of designing a drug dosage form to provide a desired drug release profile of a drug comprises: obtaining or selecting one or more fractions of the total drug released from the drug dosage form during the desired drug release profile; and subsequently obtaining the corresponding time points and/or time intervals of the desired drug release profile for each fraction of the total drug released.

The fractions or percentages of the one or more fractions or percentages of the total drug released used in the methods disclosed herein may be of any suitable size, e.g., tenth or integer values. In some embodiments, the fractions or percentages of the total drug released are based on a uniform fraction or percentage (e.g., all percentages being a single value), non-uniform fractions or percentages (e.g., including increasing percentage values), or a combination thereof.

In some embodiments, the number of the one or more fractions or percentages is based on the number of layers of a first erodible material admixed with a drug in a drug dosage form. In some embodiments, the number of fractions or percentages of the one or more fractions or percentages is between about 1 to about 100, such as between any of about 1 to about 5, about 5 to about 10, about 10 to about 15, about 5 to about 20, about 10 to about 20, about 15 to about 20, about 5 to about 500, or about 10 to about 100. In some embodiments, the number of fractions or percentages of the one or more fractions or percentages is about any of 1, 2, 3, 4, 5, 6, 7, 8, 9, 10, 11, 12, 13, 14, 15, 16, 17, 18, 19, 20, 25, 30, 35, 40, 45, 50, 75, or 100.

In some embodiments, the method of designing a drug dosage form to provide a desired drug release profile comprises evaluating an in vitro dissolution rate of the drug dosage form. In some embodiments, the desired drug release profile of a drug dosage form is similar, e.g., equivalent or bioequivalent, to the in vitro dissolution rate of the drug dosage form. In some embodiments, the desired drug release profile of a drug dosage form is similar, e.g., equivalent or bioequivalent, to the in vivo drug release profile of the drug dosage form. In some embodiments, the in vivo drug release profile of the drug dosage form is based on evaluation of the in vitro dissolution rate of the drug dosage form. In some embodiments, the desired drug release profile of a drug dosage form is similar, e.g., equivalent or bioequivalent, to a reference drug release profile. Methods for in vitro dissolution testing and determining dissolution similarity are known in the art and the U.S. Food and Drug Administration has provided industry guidance on such methods (see Guidance for Industry; Dissolution Testing of Immediate Release Solid Oral Dosage Forms; CDER; August 1997).

Methods for in vitro dissolution testing include a logarithmic curve method, probability unit method, exponential model method, Weibull method, and Gompertz method. Statistical analysis methods for determining dissolution similarity of two dissolution profiles, e.g., an experimentally determined dissolution profile and a desired drug release profile, comprise regression analysis, ANOVA, similarity factor method, varying factor method, Splitpolt method, and Chow's method. In some embodiments, the dissolution similarity is evaluated using the similarity factor. In some embodiments, the dissolution similarity is evaluated using Chow's method.

B. First Erodible Material Admixed with a Compound

The disclosure provides methods of designing a dosage form, such as an oral drug dosage form, comprising a multi-layered structure comprising a plurality of layers of a first erodible material admixed with a compound, such as a drug or a reagent, wherein the dosage form provides a desired release profile of the compound, such as a drug or a reagent. In some embodiments, the erosion of a layer of a first erodible material admixed with a drug correlates with the release rate of the drug from a drug dosage form. In some embodiments, designing a drug dosage form formulated and configured to provide a desired drug release profile comprises controlling various parameters of a layer of a first erodible material admixed with a drug, e.g., the first erodible material (which has characteristics, such as an erosion rate), thickness of the layer of the first erodible material admixed with the drug, the surface area of the layer of the first erodible material admixed with the drug, and drug mass fraction of the layer of the first erodible material admixed with the drug.

As shown in the schematic 100 of FIG. 1, a relationship exists between the time interval ($t_E$) established for the erosion of a layer of a first erodible material admixed with a drug 110, the erosion rate of the layer of the erodible material admixed with the drug 120, and thickness of the layer of the erodible material admixed with the drug 125. In some embodiments, the relationship may be expressed using Formula I:

$$v_E = \frac{H}{t_E}, \quad \text{Formula I}$$

wherein $v_E$ is the erosion rate of a layer of an erodible material, such as a layer of a first erodible material admixed with a drug, H is the thickness of the layer of the erodible material, as measured substantially in line with the direction of erosion from a surface that will first be exposed to a dissolution medium, and $t_E$ is the time interval for erosion of the layer of the erodible material. As illustrated in the schematic 100 of FIG. 1, designing a drug dosage form to provide a desired drug release profile of a drug may comprise different routes for establishing a first erodible material admixed with a drug (which has an erosion rate) 120, 130 and thickness of the layer of the first erodible material admixed with the drug 125.

In some embodiments, the method of designing a drug dosage form to provide a desired drug release profile comprises selecting a first erodible material admixed with a drug based on a hypothetical erosion rate, or range of suitable hypothetical erosion rates (such as determined based on characteristics of the size of the drug dosage form), of a layer of the first erodible material admixed with the drug. In some embodiments, the thickness of an erodible material admixed with a drug is based on the erosion rate of the selected first erodible material admixed with the drug.

In some embodiments, the method of designing a drug dosage form to provide a desired drug release profile comprises selecting a first erodible material admixed with a drug based on a hypothetical thickness, or range of suitable hypothetical thicknesses (such as a pre-determined thickness or range of thicknesses), of a layer of the first erodible material admixed with the drug. In some embodiments, the thickness of an erodible material admixed with a drug is based on the erosion rate of the selected first erodible material admixed with the drug.

In some embodiments, the method of designing a drug dosage form to provide a desired drug release profile comprises determining a thickness of a layer of a first material admixed with a drug based on pre-determination of the first material admixed with the drug, wherein the first material admixed with the drug has an erosion rate.

In some embodiments, the method of designing a drug dosage form to provide a desired drug release profile comprises adjusting the time interval for erosion of a layer of a first erodible material admixed with a drug based on the erosion rate of the first erodible material admixed with the drug and/or thickness of the layer of the first erodible material admixed with the drug.

i. First Erodible Material

The disclosure provides methods of designing a dosage form, such as an oral drug dosage form, comprising a multi-layered structure comprising a plurality of layers of a first erodible material admixed with a compound (e.g., a drug). In some embodiments, the method of designing a drug dosage form to provide a desired drug release profile comprises selecting a first erodible material admixed with a drug. In some embodiments, the first erodible material admixed with a drug is pre-determined.

In some embodiments, the erodible material comprises a thermoplastic material. In some embodiments, the erodible material is a thermoplastic material. In some embodiments, the erodible material is edible (i.e., suitable for consumption by an individual). In some embodiments, the erodible material is biocompatible (e.g., suitable for use in an implant). In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a pH sensitive polymer, a natural polymer (such as shellac), a wax-like material, and a combination thereof. In some embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, vinylpyrrolidone-vinyl acetate copolymer (VA64), polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), an (optionally alkyl-, methyl-, or ethyl-) acrylate, a methacrylate copolymer, an ethacrylate copolymer, poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), a cellulose or cellulose derivative, hydroxyl propyl cellulose (HPC), polyoxyl 40 hydrogenerated castor oil, methyl cellulose (MC), ethyl cellulose (EC), poloxamer, hydroxypropyl methylcellulose phthalate (HPMCP), poloxamer, hydrogenated castor and soybean oil, glyceryl palmitostearate, carnauba wax, polylactic acid (PLA), polyglycolic acid (PGA), cellulose acetate butyrate (CAB), colloidal silicon dioxide, a saccharide, glucose, polyvinyl acetate phthalate (PVAP), a wax, beeswax, hydrogel, gelatin, hydrogenated vegetable oil, polyvinyl acetal diethyl aminolactate (AEA), paraffin, shellac, sodium alginate, cellulose acetate phthalate (CAP), fatty oil, arabic gum, xanthan gum, glyceryl monostearate, octadecanoic acid, and a combination thereof.

In some embodiments, the erodible material comprises a non-thermoplastic material. In some embodiments, the erodible material is a non-thermoplastic material. In some embodiments, the non-thermoplastic material is selected from the group consisting of starch, pregelatinized starch, sodium starch glycolate (CMS-Na), sucrose, dextrin, lactose, microcrystalline cellulose (MCC), mannitol, magnesium stearate (MS), powdered silica gel, sodium alginate, titanium dioxide, glycerin, syrup, lecithin, soybean oil, tea oil, ethanol, propylene glycol, glycerol, Tween, animal fats, silicone oils, cacao butter, fatty acid glycerides, vaseline, chitosan, cetyl alcohol, stearyl alcohol, and a combination thereof.

In some embodiments, the erodible material comprises a plasticizer. In some embodiments, the plasticizer comprises a block copolymer of polyoxyethylene-polyoxypropylene, vitamin e polyethylene glycol succinate, hydroxystearate, polyethylene glycol (such as PEG400), macrogol cetostearyl ether 12, polyoxyl 20 cetostearyl ether, polysorbate 20, polysorbate 60, polysorbate 80, acetin, acetylated triethyl citrate, tributyl citrate, tributyl o-acetylcitrate, triethyl citrate, polyoxyl 15 hydroxystearate, peg-40 hydrogenated castor oil, polyoxyl 35 castor oil, dibutyl sebacate, diethylphthalate, glycerine, methyl 4-hydroxybenzoate, glycerol, castor oil, oleic acid, tryacetin, or polyalkylene glycol.

In some embodiments, the first erodible material admixed with a drug is a material that substantially erodes (e.g., substantially complete erosion or substantially complete dissolution) during the time a drug dosage form is in an individual. In some embodiments, substantially all of a first erodible material admixed with a drug in a drug dosage form erodes during the time the drug dosage form is in an individual. In some embodiments, substantially all of a first erodible material admixed with a drug in a drug dosage form erodes during a desired time frame that the drug dosage form is in an individual. In some embodiments, substantially all of a first erodible material admixed with a drug in a drug dosage form erodes in less than about 72 hours, such as less than about any of 66 hours, 60 hours, 54 hours, 48 hours, 42 hours, 36 hours, 30 hours, 24 hours, 18 hours, 12 hours, 10 hours, 9 hours, 8 hours, 7 hours, 6 hours, 5 hours, 4 hours, 3 hours, 2 hours, 1 hour, or 30 minutes. In some embodiments, substantially all of a first erodible material admixed with a drug in a drug dosage form erodes in about 72 hours, such about any of 66 hours, 60 hours, 54 hours, 48 hours, 42 hours, 36 hours, 30 hours, 24 hours, 18 hours, 12 hours, 10 hours, 9 hours, 8 hours, 7 hours, 6 hours, 5 hours, 4 hours, 3 hours, 2 hours, 1 hour, or 30 minutes.

In some embodiments, the erosion rate of a first erodible material admixed a drug is between about 0.1 mm/hour to about 4 mm/hour. In some embodiments, the erosion rate of a first erodible material admixed with a drug is greater than about 0.1 mm/hour, such as greater than about any of 0.2 mm/hour, 0.3 mm/hour, 0.4 mm/hour, 0.5 mm/hour, 0.6 mm/hour, 0.7 mm/hour, 0.8 mm/hour, 0.9 mm/hour, 1.0 mm/hour, 1.1 mm/hour, 1.2 mm/hour, 1.3 mm/hour, 1.4 mm/hour, 1.5 mm/hour, 1.6 mm/hour, 1.7 mm/hour, 1.8 mm/hour, 1.9 mm/hour, 2.0 mm/hour, 2.1 mm/hour, 2.2 mm/hour, 2.3 mm/hour, 2.4 mm/hour, 2.5 mm/hour, 2.6 mm/hour, 2.7 mm/hour, 2.8 mm/hour, 2.9 mm/hour, 3.0 mm/hour, 3.1 mm/hour, 3.2 mm/hour, 3.3 mm/hour, 3.4 mm/hour, 3.5 mm/hour, 3.7 mm/hour, 3.8 mm/hour, 3.9 mm/hour, or 4.0 mm/hour. In some embodiments, the erosion rate of a first erodible material admixed with a drug is less than about 0.1 mm/hour, such as less than about any of 0.2 mm/hour, 0.3 mm/hour, 0.4 mm/hour, 0.5 mm/hour, 0.6 mm/hour, 0.7 mm/hour, 0.8 mm/hour, 0.9 mm/hour, 1.0 mm/hour, 1.1 mm/hour, 1.2 mm/hour, 1.3 mm/hour, 1.4 mm/hour, 1.5 mm/hour, 1.6 mm/hour, 1.7 mm/hour, 1.8 mm/hour, 1.9 mm/hour, 2.0 mm/hour, 2.1 mm/hour, 2.2 mm/hour, 2.3 mm/hour, 2.4 mm/hour, 2.5 mm/hour, 2.6 mm/hour, 2.7 mm/hour, 2.8 mm/hour, 2.9 mm/hour, 3.0 mm/hour, 3.1 mm/hour, 3.2 mm/hour, 3.3 mm/hour, 3.4 mm/hour, 3.5 mm/hour, 3.7 mm/hour, 3.8 mm/hour, 3.9 mm/hour, or 4.0 mm/hour. In some embodiments, the erosion rate of a first erodible material admixed with a drug is about any of 0.1 mm/hour, 0.2 mm/hour, 0.3 mm/hour, 0.4 mm/hour, 0.5 mm/hour, 0.6 mm/hour, 0.7 mm/hour, 0.8 mm/hour, 0.9 mm/hour, 1.0 mm/hour, 1.1 mm/hour, 1.2 mm/hour, 1.3 mm/hour, 1.4 mm/hour, 1.5 mm/hour, 1.6 mm/hour, 1.7 mm/hour, 1.8 mm/hour, 1.9 mm/hour, 2.0 mm/hour, 2.1 mm/hour, 2.2 mm/hour, 2.3 mm/hour, 2.4 mm/hour, 2.5 mm/hour, 2.6 mm/hour, 2.7 mm/hour, 2.8 mm/hour, 2.9 mm/hour, 3.0 mm/hour, 3.1 mm/hour, 3.2 mm/hour, 3.3 mm/hour, 3.4 mm/hour, 3.5 mm/hour, 3.7 mm/hour, 3.8 mm/hour, 3.9 mm/hour, or 4.0 mm/hour.

In some embodiments, the first erodible material is suitable for admixture with a drug. In some embodiments, the first erodible material is chemically unreactive with a drug. In some embodiments, the erodible material is selected based on suitability for admixture with a drug. In some embodiments, the first erodible material is selected based on being chemically unreactive with a drug.

ii. Erosion Rate

In some embodiments, the method of designing a dosage form, such as an oral drug dosage form, to provide a desired release profile, such as a desired drug release profile, comprises obtaining, such as determining, the erosion rate ($v_E$) of an erodible material, such as a first erodible material admixed with a drug.

The erosion rate of an erodible material can be obtained, such as determined or measured, by methods known in the art or, for example, the methods disclosed herein. In some embodiments, the erosion rate ($v_E$) of an erodible material, such as a layer of a first erodible material admixed with a drug, may be obtained using Formula I.

In some embodiments, obtaining the erosion rate ($v_E$) of a first erodible material admixed with a drug comprises using a dye form, such as methylene blue powder, to indicate when a certain thickness of the first erodible material has eroded to release the dye form into solution, such as a dissolution medium. In some embodiments, the dissolution medium replicates in vivo conditions. In some embodiments, the dissolution medium is selected from the group consisting of hydrochloric acid buffer, acid phthalate buffer, neutralized phthalate buffer, phosphate buffer, alkaline borate buffer, acetate buffer, simulated intestinal fluid, simulated gastric fluid, and a combination thereof. In some embodiments, the dissolution medium is stirred or agitated. In some embodiments, the dissolution medium is maintained at a temperature of about 37° C. For example, if a layer of a first erodible material admixed with a drug having a thickness of 1 mm (as measured substantially in line with the direction of erosion from a top surface of the erodible material exposed to a dissolution medium to a groove containing the dye form) erodes and releases the dye form into the dissolution medium in 2 hours, then the erosion rate ($v_E$) of the first erodible material admixed with a drug is 0.5 mm/hour.

In some embodiments, obtaining the erosion rate of a first erodible material admixed with a drug comprises obtaining the erosion rate of the first material admixed with a substitute drug. In some embodiments, the substitute drug and the drug have one or more similar chemical properties, e.g., molecular weight, hydrophilicity, hydrophobicity, functional groups, and/or core structure.

In some embodiments, Formula I may be used to obtain the erosion rate ($v_E$) of a first erodible material admixed with a drug, wherein the drug is homogenously admixed with the erodible material. In some embodiments, Formula I may be used to obtain the erosion rate ($v_E$) of a first erodible material admixed with a drug, wherein for a thickness of the erodible material the drug forms a gradient substantially in line with the thickness of the erodible material.

In some embodiments, the erosion rate ($v_E$) of a first erodible material admixed with a drug may be obtained with data from a first time point ($t_1$) and a subsequent second time point ($t_2$) using Formula II:

$$v_E = \frac{(\%_{t2} * H) - (\%_{t1} * H)}{t_2 - t_1},$$ Formula II, wherein H is the thickness of the erodible material prior to erosion, $\%_{t1}$ is the percentage, in decimal form, of the drug in solution at $t_1$, and wherein $\%_{t2}$ is the percentage, in decimal form, of the drug in solution at $t_2$. In some embodiments, the volume of a dissolution medium comprising a drug removed at a time point, for purposes of measuring the amount of the drug in solution, is replaced with dissolution medium following removal.

In some embodiments, Formula II may be used to obtain the erosion rate ($v_E$) of a first erodible material admixed with a drug, wherein the drug is homogenously admixed with the first erodible material.

In some embodiments, the drug and/or another non-drug agent admixed with a first erodible material alters the erosion rate of the first erodible material not admixed with the drug. For example, properties of a drug and/or amount of the drug, such as high drug mass fractions, admixed in a first erodible material may alter the erosion rate of the first erodible material admixed with the drug as compared to the first erodible material not admixed with the drug. In some embodiments, the methods of designing a drug dosage form to provide a desired drug release profile comprise obtaining, such as determining or measuring, erosion rates of a first material admixed with a plurality of amounts of a drug. In some embodiments, the erosion rate of a first erodible material admixed with a drug is the same as the first erodible material not admixed with the drug. In some embodiments, the erosion rate of a first erodible material admixed with a drug is different than the first erodible material not admixed with the drug.

In some embodiments, obtaining the erosion rate of an erodible material, such as a first erodible material admixed with a drug, comprises performing multiple assessments of the erodible material, e.g., with varying thicknesses, replicates, and different dissolution media.

In some embodiments, the method of designing a drug dosage form to provide a desired drug release profile of a drug comprises creating a database comprising at least one property of a first erodible material admixed with a drug, e.g., erosion rate. In some embodiments, the at least one property comprises the erosion rate of a first erodible material admixed with a drug.

In some embodiments, erosion rates of a first erodible material admixed with a drug may be obtained from the art or a database. In some embodiments, the method of designing a drug dosage form to provide a desired drug release profile comprises obtaining the erosion rate ($v_E$) of a first erodible material admixed with a drug from a database. In some embodiments, the method of designing a drug dosage form to provide a desired drug release profile comprises selecting a first erodible material admixed with a drug from a database.

In some embodiments, the method of designing a drug dosage form to provide a desired drug release profile comprises selecting a first erodible material admixed with a drug, wherein the first erodible material is selected based on a property of the first erodible material or the first erodible material admixed with the drug. In some embodiments, selecting a first erodible material admixed with a drug is based on the erosion rate of the first erodible material admixed with the drug.

In some embodiments, the method of designing a drug dosage form to provide a desired drug release profile comprises selecting a first erodible material admixed with a drug based on a hypothetical erosion rate, or range of hypothetical erosion rates, of a layer of the first erodible material admixed with the drug. In some embodiments, the hypothetical erosion rate, or range of hypothetical erosion rates, of a first erodible material admixed with a drug is based on suitable erosion rates that will provide a desired rug release profile. In some embodiments, the hypothetical erosion rate, or range of hypothetical erosion rates, of a first erodible material admixed with a drug is based on correlating erosion rates with the size of a drug dosage form. In some embodiments, the hypothetical erosion rate, or range of hypothetical erosion rates, of a first erodible material admixed with a drug is based on erosion rates that satisfy Formula I based on the size of a drug dosage form, such as the maximum size of the drug dosage form.

In some embodiments, the method of designing a drug dosage form to provide a desired drug release profile comprises selecting a first erodible material admixed with a drug from a plurality of erodible materials admixed with the drug having a property that satisfies a hypothetical desired property.

In some embodiments, the method of designing a drug dosage form to provide a desired drug release profile comprises using a first erodible material admixed with a drug that is pre-determined.

iii. Thickness

In some embodiments, the method of designing a dosage form, such as a drug dosage form, to provide a desired release profile, such as a desired drug release profile, comprises obtaining, such as determining, thickness of an erodible material, such as a first erodible material admixed with a drug.

In some embodiments, based on Formula I, the thickness (H) of a layer of an erodible material, such as a first erodible material admixed with a drug, is obtained using Formula III:

$$H = t_E \times v_E,$$ Formula III, wherein $t_E$ is the total time of erosion of the layer of the erodible material and $v_E$ is the erosion rate of the erodible material.

In some embodiments, the method of designing a drug dosage form to provide a desired drug release profile comprises determining a thickness of a layer of a first material admixed with a drug based on the first material admixed with the drug, wherein the first material admixed with the drug has an erosion rate. In some embodiments, the method of designing a drug dosage form to provide a desired drug release profile comprises determining a thickness of a layer of a first material admixed with a drug based on pre-determination of the first material admixed with the drug, wherein the first material admixed with the drug has an erosion rate.

In some embodiments, the method of designing a drug dosage form to provide a desired drug release profile comprises selecting a first erodible material admixed with a drug based on a hypothetical thickness, or range of suitable hypothetical thicknesses (such as a pre-determined thickness or range of thicknesses), of a layer of the first erodible material admixed with the drug. In some embodiments, the hypothetical thickness of a layer of a first erodible material admixed with a drug is used to obtain a hypothetical erosion rate of the first erodible material admixed with the drug. In some embodiments, the hypothetical erosion rate is then used to select a first erodible material admixed with a drug, wherein the first erodible material admixed with the drug has an erosion rate. In some embodiments, the hypothetical erosion rate and the erosion rate of a first erodible material admixed with a drug are the same. In some embodiments, the hypothetical erosion rate and the erosion rate of a first erodible material admixed with a drug are different. In some embodiments, the erosion rate of a first erodible material admixed with a drug is then used to obtain a thickness of the first erodible material admixed with the drug. In some embodiments, the hypothetical thickness and thickness of a first erodible material admixed with a drug are the same. In some embodiments, the hypothetical thickness and thickness of a first erodible material admixed with a drug are different.

In some embodiments, the hypothetical thickness, or range of hypothetical thicknesses, of a layer of a first erodible material admixed with a drug is based on the size of a drug dosage form, number of layers in the drug dosage form, the printable resolution of a layer in the drug dosage form (e.g., the minimum printable thickens), a desired drug release profile of the drug dosage form, or a combination thereof. In some embodiments, the hypothetical thickness, or range of hypothetical thicknesses, of a layer of a first erodible material admixed with a drug is based on thicknesses that satisfy Formula I.

FIG. 2A shows a drug dosage form 200 having three layers of a first erodible material admixed with a drug 215, 220, 225, wherein the thickness of a layer 220, as measured substantially in line with the direction of erosion 230, is indicated 235. In some embodiments, when a first erodible material admixed with a drug having a known erosion rate is selected, e.g., pre-selected, the thickness 235 of a layer of the erodible material admixed with the drug 220 may be calculated according to Formula III (FIG. 2A). In some embodiments, a hypothetical thickness, or range of hypothetical thickness, based on a first model of a drug dosage form 200 may be used to select a first erodible material admixed with a drug having an erosion rate, wherein the erosion rate of the first erodible material admixed with a drug is used to calculate the thickness 235 of a layer of the erodible material admixed with the drug 220 according to Formula III (FIG. 2A).

iv. Mass Fraction and Surface Area of a Layer of a First Erodible Material Admixed with a Compound As shown in the schematic 100 of FIG. 1, a relationship exists between the mass fraction, such as drug mass fraction, of a layer of a first erodible material admixed with a compound a compound (e.g., a drug) or reagent, 135 of a dosage form, such as a drug dosage form, and the surface area of the layer of the first erodible material admixed with the compound (e.g., the drug) or reagent 140.

In some embodiments, the drug mass fraction ($m_F$) of a drug in a layer of an erodible material admixed with the drug is obtained using Formula IV:

$$m_F = \frac{m_D}{m_{Tot}}, \qquad \text{Formula IV,}$$

wherein $m_D$ is the mass of the drug in the layer of the erodible material admixed with the drug, and wherein $m_{Tot}$ is the total mass of the layer of the erodible material admixed with the drug.

In some embodiments, based on, e.g., Formula IV, the relationship between the drug mass fraction of a layer of a first erodible material admixed with a drug and the volume of the layer ($V_{vol}$) of the first erodible material admixed with the drug is based on Formula V:

$$m_F = \frac{\%_L * m_{DTot}}{\rho * V_{vol}}, \qquad \text{Formula V,}$$

wherein $m_F$ is the drug mass fraction of the drug in the layer of the first erodible material admixed with the drug, $\%_L$ is the percentage, in decimal form, of the total drug in the drug dosage form that is in the layer of the erodible material admixed with the drug, $m_{DTot}$ is the total mass of the drug in the drug dosage form, and $\rho$ is the density of the layer of the erodible material admixed with the drug. In some embodiments, mathematically equivalent terms may be substituted for terms recited in Formula V. For example, in some embodiments, when the shape of a layer of a first erodible material admixed with a drug allows, such as for a cylinder, $V_{vol}$ can be substituted with thickness (H) of the layer of the first erodible material admixed with the drug multiplied by the surface area (S) of the layer of the first erodible material admixed with the drug.

In some embodiments, when the total mass of a drug in a drug dosage form, the percentage of the total drug in a layer of an erodible material admixed with the drug, and thickness of the layer of the erodible material admixed with the drug are held constant for a first layer and a second layer, the first layer, which has a higher drug $m_F$ in the layer as compared to the second layer, may have the same desired drug release profile as the second layer if the first layer has a smaller surface area as compared to the second layer.

As illustrated in the schematic 100 of FIG. 1, designing a drug dosage form to provide a desired drug release profile of a drug may comprise different routes for establishing the drug mass fraction of a layer of a first erodible material admixed with a drug 135 and the surface area of the layer of the first erodible material admixed with the drug 140.

In some embodiments, the method of designing a drug dosage form with a desired drug release profile comprises obtaining, such as determining or selecting, a hypothetical surface area, or range of hypothetical surface areas, of a layer of a first erodible material admixed with a drug. In some embodiments, the hypothetical surface area, or range of hypothetical surface areas, of a layer of a first erodible material admixed with a drug is based on the size of a drug dosage form, e.g., the maximum and minimum size of a drug dosage form. In some embodiments, the method of designing a drug dosage form with a desired drug release profile comprises obtaining a hypothetical drug mass fraction, or range of hypothetical drug mass fractions, of a layer of a first erodible material admixed with a drug based on a hypothetical surface area, or range of hypothetical surface areas, of the layer of the first erodible material admixed with the drug. In some embodiments, the method of designing a drug dosage form with a desired drug release profile comprises obtaining, such as selecting, a drug mass fraction of a layer of a first erodible material admixed with a drug based on a hypothetical drug mass fraction, or range of hypothetical drug mass fractions, of the layer of the first erodible material admixed with the drug. In some embodiments, the drug mass fraction of a layer of a first erodible material admixed with a drug is selected based on a property of the first erodible material admixed with the drug, e.g., erosion rate. In some embodiments, the erosion rate of a first erodible material is the same as the erosion rate of the first material admixed with a drug, wherein the drug is present in the first erodible material admixed with the drug at the selected drug mass fraction. In some embodiments, method of designing a drug dosage form with a desired drug release profile comprises obtaining the surface area of a layer of a first erodible material admixed with a drug based on the selected drug mass fraction of the first erodible material admixed with the drug.

In some embodiments, the method of designing a drug dosage form with a desired drug release profile comprises obtaining, such as determining or selecting, a hypothetical drug mass fraction area, or range of hypothetical drug mass fractions, of a layer of a first erodible material admixed with a drug. In some embodiments, the hypothetical drug mass fraction, or range of hypothetical drug mass fraction, of a layer of a first erodible material admixed with a drug is based on a property of the first erodible material admixed with the drug, e.g., erosion rate. In some embodiments, the erosion rate of a first erodible material is the same as the erosion rate of the first material admixed with a drug, wherein the drug is present in the first erodible material admixed with the drug at the hypothetical drug mass fraction, or range of hypothetical drug mass fractions. In some embodiments, the method of designing a drug dosage form with a desired drug release profile comprises obtaining a hypothetical surface area, or range of hypothetical surface areas, of a layer of a first erodible material admixed with a drug based on a hypothetical drug mass fraction, or range of hypothetical drug mass fraction, of the layer of the first erodible material admixed with the drug. In some embodiments, the method of designing a drug dosage form with a desired drug release profile comprises obtaining, such as selecting, a surface area of a layer of a first erodible material admixed with a drug based on a surface area, or range of hypothetical surface areas, of the layer of the first erodible material admixed with the drug. In some embodiments, the surface of a layer of a first erodible material admixed with a drug is selected based on a property of a drug dosage form, e.g., size. In some embodiments, method of designing a drug dosage form with a desired drug release profile comprises obtaining the drug mass fraction of a layer of a first erodible material admixed with a drug based on the selected surface area of the first erodible material admixed with the drug.

Figure 2B:
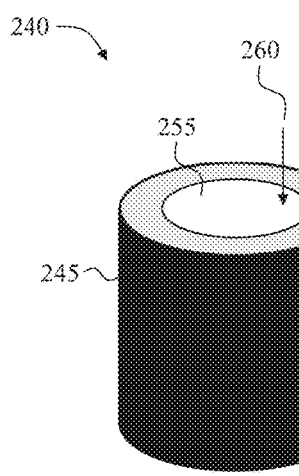
Figure 2C:
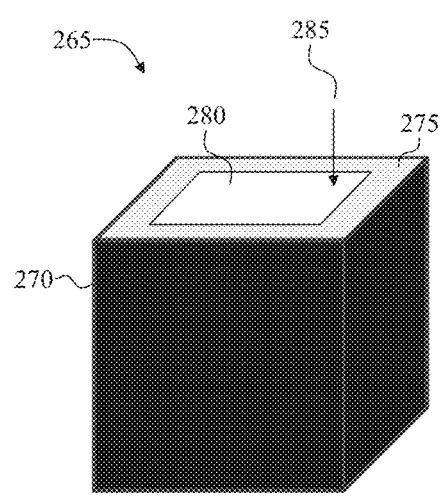

As disclosed herein, the methods of designing a dosage form, such as a drug dosage form, with a desired release profile, such as a desired drug release profile, may have a surface area of a layer of a first erodible material admixed with a compound (e.g., a drug) of any shape suitable for 3D printing of a dosage form. For example, the drug dosage form 240 illustrated in FIG. 2B may have the same desired drug release profile of the drug dosage form 265 illustrated in FIG. 2C, where the surface area of a layer of a first erodible material 255 in the drug dosage form 240 of FIG. 2B is a circle and the surface area of a layer of a first erodible material 280 in the drug dosage form 265 of FIG. 2C is a square.

Figure 3A:
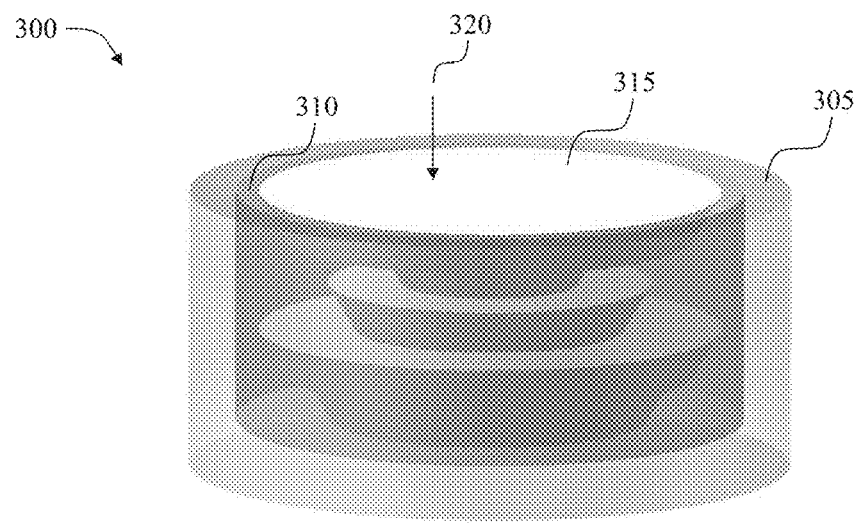
FIGS. 3A-3B show an exemplary drug dosage form 300.
Figure 3B:
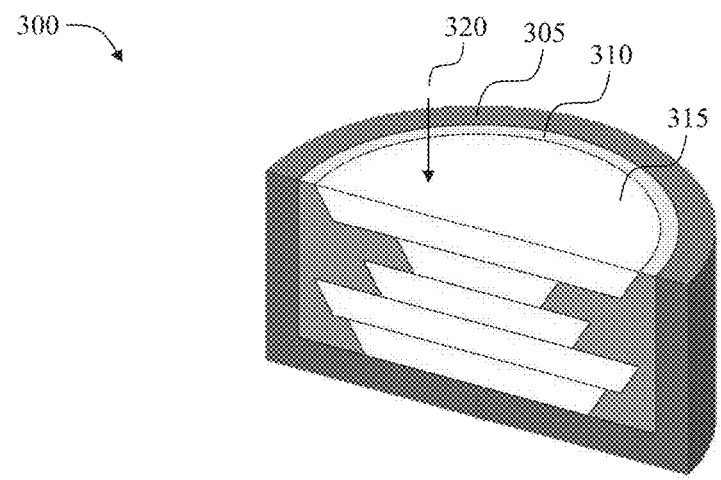

As illustrated in FIG. 3A and FIG. 3B, a drug dosage form 300 with a desired drug release profile comprising a multi-layered structure comprising a plurality of layers of a first erodible material admixed with the drug 315, wherein the first erodible material embedded in a second material not admixed with the drug 310 may comprise the plurality of layers of similar surface area shapes and/or tapers.

Figure 4A:
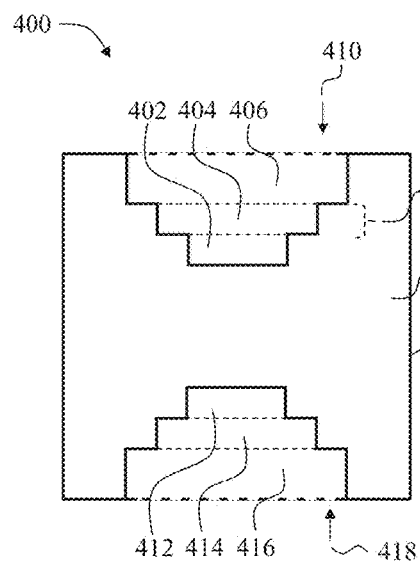
FIGS. 4A-4C show exemplary drug dosage forms 400, 425 formulated and configured to provide a desired drug release profile.
Figure 4B:
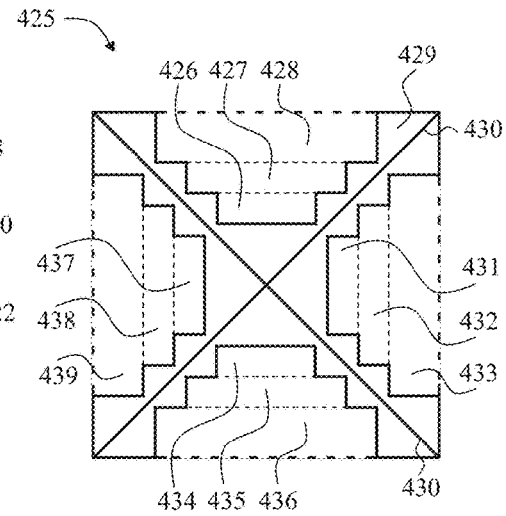
Figure 4C:
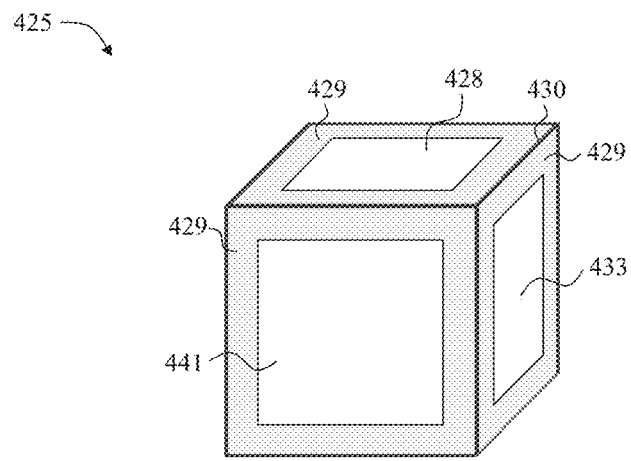

In some embodiments, the method of designing a drug dosage form with a desired drug release profile comprises separating, e.g., partitioning, an obtained surface area of a layer of a first erodible material admixed with a drug. In some embodiments, the surface area of a layer of a first erodible material admixed with a drug is continuous. In some embodiments, the surface area of a layer of a first erodible material admixed with a drug is discontinuous. For example, as illustrated in the exemplary oral dosage forms of FIGS. 4A-4C, a multi-layered structure comprising a plurality of layers of a first erodible material admixed with a drug, wherein the first erodible material embedded in a second material may have more than one layer of the first erodible material admixed with a drug simultaneously exposed to a solution, such as bodily fluid, e.g., gastrointestinal (GI) fluid. As illustrated in FIG. 4A, the drug dosage form 400 comprising a multi-layered structure comprising a plurality of layers of a first erodible material admixed with a drug embedded in a second material not admixed with the drug 420 comprise six layers 402, 404, 406, 412, 414, 416 of the first erodible material admixed with the drug, wherein at least a first layer 406 and a second layer 416 are simultaneously exposed to a solution following administration. As illustrated in FIGS. 4B-4C, the drug dosage form 425 comprising a multi-layered structure comprising a plurality of layers of a first erodible material admixed with a drug embedded in a second material not admixed with the drug 429 comprises 18 layers of the first erodible material admixed with the drug (12 layers are shown in FIG. 4B: 426-428, 431-439), wherein, as labeled in FIG. 4C, six layers, including a first layer 428, a second layer 433, and a third layer 441, are simultaneously exposed to a solution following administration.

In some embodiments, the surface of a layer of a first erodible material admixed with a drug is designed to control the surface area exposed to a solution, such as bodily fluid, e.g., gastrointestinal (GI) fluid. In some embodiments, the surface of a layer of a first erodible material admixed with a drug is designed to increase the surface area exposed to a solution, as compared to a planar surface of the same dimensions. In some embodiments, the surface of a layer of a first erodible material admixed with a drug is planar (e.g., FIG. 2A-4C). In some embodiments, the surface of a layer of a first erodible material admixed with a drug is curved (e.g., FIG. 5 and FIG. 6). In some embodiments, the surface of a layer of a first erodible material admixed with a drug comprises at least one projection, such as villi.

For use in Formula V, in some embodiments, density ($\rho$) of a layer of an erodible material, whether or not admixed with a drug, is obtained using Formula VI:

$$\rho = \frac{m}{v_{vol}}, \quad \text{Formula VI,}$$

wherein, when the erodible material is not admixed with the drug, m is the total mass of the layer of the erodible material not admixed with the drug, wherein, when the erodible material is admixed with the drug, m is the total mass of the layer of the erodible material admixed with the drug (including the mass of the drug), and wherein $V_{vol}$ is the volume of the layer.

In some embodiments, the method of designing a drug dosage form to provide a desired drug release profile comprises adjusting the pre-determine parameters of a layer comprising a first erodible material admixed with a drug, e.g., surface area, thickness, drug mass fraction, to create new parameters for the layer, wherein an equal amount of the drug is released from the prior layer parameters and the adjusted layer parameters over the erosion time of the layers. In some embodiments, the layer is a layer of a multi-layered structure of a drug dosage form. In some embodiments, the layer is the top layer of a multi-layered structure of a drug dosage form.

Figure 7:
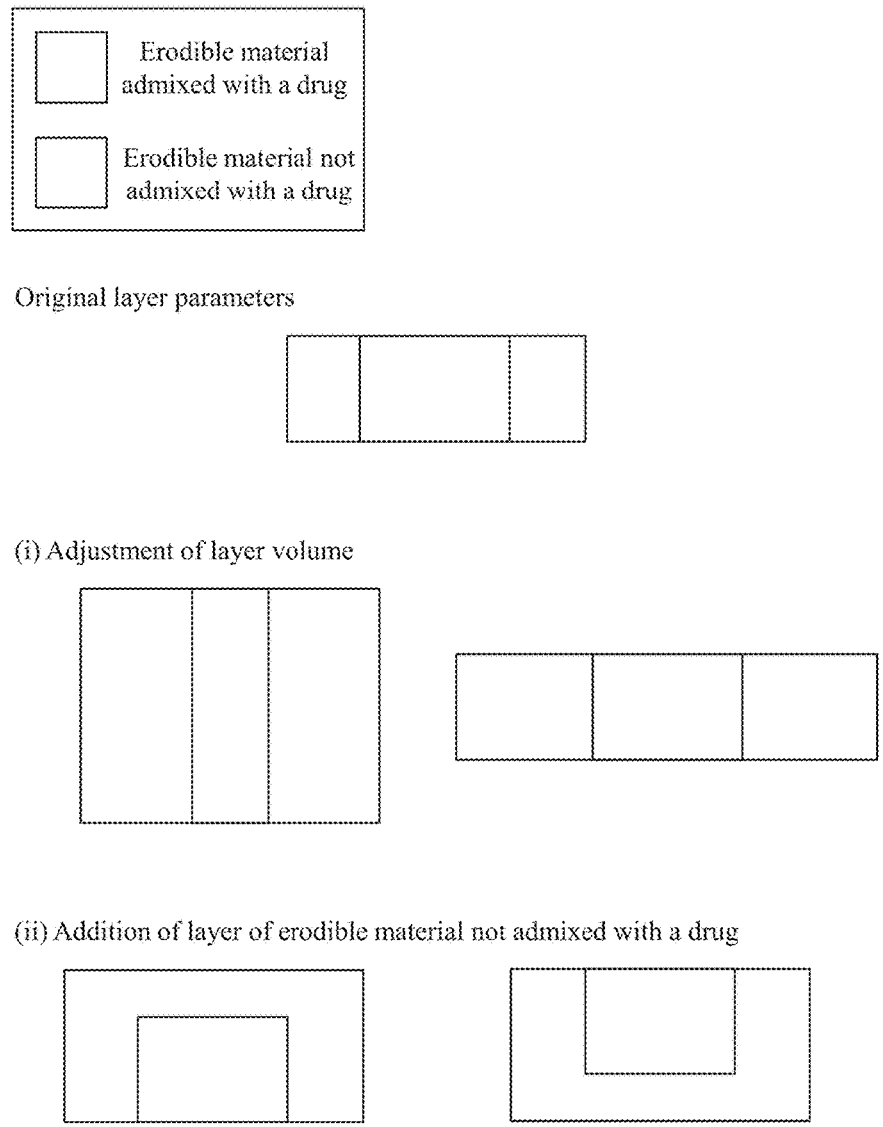
FIG. 7 shows a schematic of techniques for modulating a layer of an erodible material admixed with a drug.

In some embodiments, the volume of the layer is adjusted. In some embodiments, the volume of the layer is increased. In some embodiments, the top layer of the multi-layered structure is increased in volume. In some embodiments, the relative amount of a drug per amount of material in the adjusted layer is less than in the layer prior to adjustment. For example, as shown in FIG. 7, the original layer parameters provide a layer comprising a first erodible material admixed with a drug embedded in a second erodible material not admixed with the drug. In some embodiments, the original layer parameters are adjusted to increase the thickness of the original layer, wherein the relative amount of the drug in the layer (layer includes the first erodible material and second erodible material) after adjustment is decreased as compared to the layer prior to adjustment. In some embodiments, the original layer parameters are adjusted to increase the volume of the second erodible material not admixed with the drug.

In some embodiments, the layer comprising a first erodible material admixed with a drug is adjusted by adding one or more additional layers of a second erodible material not admixed with the drug. For example, as shown in FIG. 7, an additional layer of a second erodible material not admixed with the drug may be added on top of or below the layer comprising a first erodible material admixed with the drug. In some embodiments, a layer of a second erodible material not admixed with a drug is added above the top layer comprising a first erodible material admixed with the drug of a multi-layered structure. In some embodiments, a layer of a second erodible material not admixed with a drug is added directly below the top layer comprising a first erodible material admixed with the drug of a multi-layered structure.

In some embodiments, the layer comprising a first erodible material admixed with a drug is adjusted by selecting a substitute erodible material, wherein the parameters of the layer are adjusted according to the erosion rate of the substitute erodible material. In some embodiments, the substitute erodible material has a slower erosion rate than the first erodible material. In some embodiments, the substitute erodible material has a faster erosion rate than the first erodible material. In some embodiments, the top layer comprising a first erodible material admixed with a drug of a multi-layered structure is adjusted by selecting a substitute erodible material to admixed with the drug. In some embodiments, the top layer comprising a first erodible material admixed with a drug of a multi-layered structure is adjusted by selecting a substitute erodible material to admixed with the drug, wherein the substitute erodible material has a slower erosion rate than the first erodible material. In some embodiments, the top layer comprising a first erodible material admixed with a drug of a multi-layered structure is adjusted by selecting a substitute erodible material to admixed with the drug, wherein the substitute erodible material has a faster erosion rate than the first erodible material.

In some embodiments, the top n number of layers of a multi-layered structure are adjusted by merging the top n number of layers into a single layer with parameters that will meet the desired drug release profile of the top n number of layers.

It will be understood by those skilled in the art that the methods provided herein also encompass methods of printing and designing based on one or more of the adjusted parameters discussed herein.

C. Second Erodible Material not Admixed with a Compound

The present disclosure provides methods of designing a dosage form, such as an oral drug dosage form, to provide a desired release profile, such as a desired drug release profile, wherein the dosage form comprises a multi-layered structure comprising a plurality of layers of a first erodible material admixed with a compound a compound (e.g., a drug) or reagent, wherein the first erodible material is embedded in a second material not admixed with the compound (e.g., the drug) or reagent. In some embodiments, the method of designing a drug dosage form to provide a desired drug release profile comprises selecting a second material not admixed with a drug. In some embodiments, the second material not admixed with a drug is pre-determined.

In some embodiments, the second material comprises a thermoplastic material. In some embodiments, the second material is a thermoplastic material. In some embodiments, the second material is edible (i.e., suitable for consumption by an individual). In some embodiments, the second material is biocompatible (e.g., suitable for use in an implant). In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a non-erodible polymer, a pH sensitive polymer, a natural polymer (such as shellac), a wax-like material, and a combination thereof.

In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a pH sensitive polymer, a natural polymer (such as shellac), a wax-like material, and a combination thereof. In some embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), an (optionally alkyl-, methyl-, or ethyl-) acrylate, a methacrylate copolymer, an ethacrylate copolymer, poly(butyl methacrylate-co-(2-dimethylaminoethyl) methacrylate-co-methyl methacrylate) 1:2:1, poly(dimethylaminoethylmethacrylate-co-methacrylic esters), poly (ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly (methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly (ethylene-co-vinyl acetate), ethylene-vinyl acetate copolymer, polyethylene (PE), and polycaprolactone (PCL), hydroxyl propyl cellulose (HPC), polyoxyl 40 hydrogenerated castor oil, methyl cellulose (MC), ethyl cellulose (EC), poloxamer, hydroxypropyl methylcellulose phthalate (HPMCP), poloxamer, hydrogenated castor and soybean oil, glyceryl palmitostearate, carnauba wax, polylactic acid (PLA), polyglycolic acid (PGA), a cellulose or cellulose derivative, cellulose acetate butyrate (CAB), colloidal silicon dioxide, a saccharide, glucose, polyvinyl acetate phthalate (PVAP), a wax, beeswax, hydrogel, gelatin, hydrogenated vegetable oil, polyvinyl acetal diethyl aminolactate (AEA), paraffin, shellac, sodium alginate, cellulose acetate phthalate (CAP), fatty oil, arabic gum, xanthan gum, glyceryl monostearate, octadecanoic acid, and a combination thereof.

In some embodiments, the second material comprises a non-thermoplastic material. In some embodiments, the second material is a non-thermoplastic material. In some embodiments, the non-thermoplastic material is selected from the group consisting of starch, pregelatinized starch, sodium starch glycolate (CMS-Na), sucrose, dextrin, lactose, microcrystalline cellulose (MCC), mannitol, magnesium stearate (MS), powdered silica gel, sodium alginate, titanium dioxide, glycerin, syrup, lecithin, soybean oil, tea oil, ethanol, propylene glycol, glycerol, Tween, animal fats, silicone oils, cacao butter, fatty acid glycerides, vaseline, chitosan, cetyl alcohol, stearyl alcohol, and a combination thereof.

In some embodiments, the second material comprises a plasticizer. In some embodiments, the plasticizer comprises a block copolymer of polyoxyethylene-polyoxypropylene, vitamin e polyethylene glycol succinate, hydroxystearate, polyethylene glycol (such as PEG400), macrogol cetostearyl ether 12, polyoxyl 20 cetostearyl ether, polysorbate 20, polysorbate 60, polysorbate 80, acetin, acetylated triethyl citrate, tributyl citrate, tributyl o-acetylcitrate, triethyl citrate, polyoxyl 15 hydroxystearate, peg-40 hydrogenated castor oil, polyoxyl 35 castor oil, dibutyl sebacate, diethylphthalate, glycerine, methyl 4-hydroxybenzoate, glycerol, castor oil, oleic acid, tryacetin, or polyalkylene glycol.

In some embodiments, the method of designing a drug dosage form to provide a desired drug release profile comprises selecting a second material not admixed with a drug. In some embodiments, the method of designing a drug dosage form to provide a desired drug release profile comprises selecting: (a) a first erodible material admixed with a drug; and (b) a second material not admixed with a drug. In some embodiments, the first erodible material admixed with a drug and a second material not admixed with the drug are the same. In some embodiments, the second material not admixed with a drug is an erodible material, such as a second erodible material. In some embodiments, the first erodible material admixed with a drug and the second material not admixed with the drug are the same, wherein the second material is a second erodible material. In some embodiments, the first erodible material admixed with a drug and the second material not admixed with the drug are different, wherein the second material is a second erodible material.

In some embodiments, the second material not admixed with a drug, wherein the second material is a second erodible material, is a material that erodes (e.g., completely erodes or undergoes complete dissolution) during the time a drug dosage form is in an individual. In some embodiments, the second material not admixed with a drug, wherein the second material is a second erodible material, is a material that does not completely erode during the time a drug dosage form is in an individual.

In some embodiments, the method of designing a drug dosage form to provide a desired drug release profile comprises selecting a second material not admixed with a drug, wherein the second material is a second erodible material, and wherein the second erodible material is selected based on a property of the second erodible material. In some embodiments, selecting a second material not admixed with a drug, wherein the second material is a second erodible material, is based on the erosion rate of the second erodible material.

In some embodiments, the method of designing a drug dosage form to provide a desired drug release profile comprises selecting: (a) a first erodible material admixed with a drug; and (b) a second material not admixed with a drug, wherein the second material is a second erodible material, and wherein selection of the second material is based on the erosion rate of the first erodible material. In some embodiments, the method of designing a drug dosage form to provide a desired drug release profile comprises selecting: (a) a first erodible material admixed with a drug; and (b) a second material not admixed with a drug, wherein the second material is a second erodible material, and wherein selection of the first erodible material is based on the erosion rate of the second erodible material. In some embodiments, the erosion rate of a second material not admixed with a drug, wherein the second material is a second erodible material, is selected to control the exposure of a layer of a first erodible material admixed with the drug to a dissolution medium. In some embodiments, the erosion rate of a first erodible material admixed with a drug and a second material not admixed with a drug, wherein the second material is a second erodible material, is the same. In some embodiments, the erosion rate of a first erodible material admixed with a drug and a second material not admixed with a drug, wherein the second material is a second erodible material, is different. In some embodiments, the erosion rate of a first erodible material admixed with a drug is faster than a second material not admixed with a drug, wherein the second material is a second erodible material. In some embodiments, the erosion rate of a first erodible material admixed with a drug is slower than a second material not admixed with a drug, wherein the second material is a second erodible material.

For example, in the drug dosage form 200 illustrated in FIG. 2A, a second material not admixed with a drug 210 may be selected based on the erosion rate of the second material, wherein each layer of a first erodible material admixed with the drug 215, 220, 225 is exposed to solution with the desired surface area to provide the desired drug release profile, e.g., for the second layer of the first erodible material admixed with the drug 220, only the top surface area (i.e., not the sides where, e.g., thickness is indicated 235) is exposed to solution after the first layer of the first erodible material admixed with the drug 215 dissolves.

In some embodiments, the second material is an enteric material. In some embodiments, the first erodible material is embedded in the second material, wherein the second material is an enteric material, and wherein the second material encapsulates the first material. The term "encapsulates," as used herein, encompasses embodiments wherein the second material fully encapsulates (e.g., encloses) the first material and embodiments wherein the second material partially encapsulates the first material (e.g., via a plug comprising the second material). In some embodiments, the first erodible material is embedded in the second material, wherein the second material is an enteric material, and wherein the second material fully encapsulates the first material. In some embodiments, the first erodible material is embedded in the second material, wherein the second material is an enteric material, and wherein the second material partially encapsulates the first material. In some embodiments, the first erodible material is embedded in the second material, wherein the second material is an enteric material, and wherein the second material forms a plug.

Figure 8A:
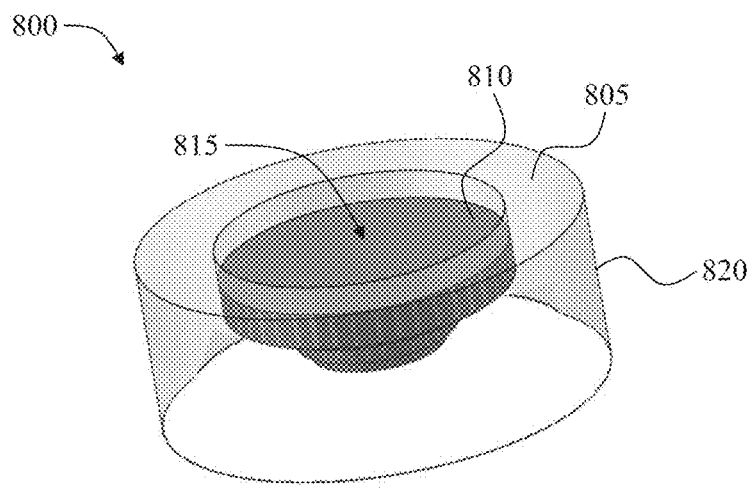
FIGS. 8A-8B show an exemplary drug dosage form 800.

In some embodiments, the method of designing a drug dosage form to provide a desired drug release profile comprises designing a layer of a second material not admixed with the drug that forms a rim, wherein the rim forms a space, and wherein the space is on top of a multi-layered structure comprising a plurality of layers of a first erodible material admixed with a drug. The top of the multi-layered structure refers to the layer of the first erodible material admixed with a drug of the multi-layered structure that is first contacted with bodily fluid, such as gastrointestinal fluid, upon oral administration. For example, as shown in FIG. 8A, the exemplary drug dosage form 800 comprises a second material that forms a rim 805 above the top of the multi-layered structure comprising a plurality of layers of the first erodible material admixed with the drug 810. The rim form the space 815 shown in FIG. 8A. In some embodiments, the space is not filled with a material. In some embodiments, the space is filled with another erodible material, e.g., another erodible material admixed with a different drug.

In some embodiments, the method of designing a drug dosage form to provide a desired drug release profile comprises obtaining, such as selecting, a thickness (as measured substantially in line with the direction of erosion from the top of the multi-layered structure to the most exterior surface of the rim) of a rim formed by a second material not admixed with the drug. In some embodiments, the thickness of the rim is at least about 0.01 mm, such as at least about any of 0.05 mm, 0.1 mm, 0.15 mm, 0.2 mm, 0.25 mm, 0.3 mm, 0.35 mm, 0.4 mm, 0.45, 0.5 mm, 0.55 mm, 0.6 mm, 0.65 mm, 0.7 mm, 0.75 mm, 0.8 mm, 0.85 mm, 0.9 mm 0.95 mm, or 1 mm. In some embodiments, the thickness of the rim is about any of 0.01 mm, 0.05 mm, 0.1 mm, 0.15 mm, 0.2 mm, 0.25 mm, 0.3 mm, 0.35 mm, 0.4 mm, 0.45, 0.5 mm, 0.55 mm, 0.6 mm, 0.65 mm, 0.7 mm, 0.75 mm, 0.8 mm, 0.85 mm, 0.9 mm 0.95 mm, or 1 mm. In some embodiments, the thickness of the rim is about 0.52 mm.

D. Intermediate Material not Admixed with a Compound

The present disclosure provides methods of designing a dosage form, such as an oral drug dosage form, to provide a desired release profile, such as a desired drug release profile, wherein the dosage form comprises a multi-layered structure comprising a plurality of layers of a first erodible material admixed with a compound a compound (e.g., a drug) or reagent, wherein the first erodible material is embedded in a second material not admixed with the compound (e.g., the drug) or reagent, and wherein an intermediate material not admixed with the compound (e.g., the drug) or reagent forms an intermediate layer between two or more layers of the first erodible material. In some embodiments, the intermediate material is an erodible material. In some embodiments, the intermediate material is an erodible material, wherein the intermediate material forms a plug. In some embodiments, the method of designing a drug dosage form to provide a desired drug release profile comprises selecting an intermediate material not admixed with a drug, wherein the intermediate material is an erodible material. In some embodiments, the intermediate material not admixed with a drug is pre-determined, wherein the intermediate material is an erodible material.

In some embodiments, the intermediate material comprises a thermoplastic material. In some embodiments, the intermediate material is a thermoplastic material. In some embodiments, the intermediate material is edible (i.e., suitable for consumption by an individual). In some embodiments, the intermediate material is biocompatible (e.g., suitable for use in an implant). In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a non-erodible polymer, a pH sensitive polymer, a natural polymer (such as shellac), a wax-like material, and a combination thereof.

In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a pH sensitive polymer, a natural polymer (such as shellac), a wax-like material, and a combination thereof. In some embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), an (optionally alkyl-, methyl-, or ethyl-) acrylate, a methacrylate copolymer, an ethacrylate copolymer, poly(butyl methacrylate-co-(2-dimethylaminoethyl) methacrylate-co-methyl methacrylate) 1:2:1, poly(dimethylaminoethylmethacrylate-co-methacrylic esters), poly (ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly (methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly (ethylene-co-vinyl acetate), ethylene-vinyl acetate copolymer, polyethylene (PE), and polycaprolactone (PCL), hydroxyl propyl cellulose (HPC), polyoxyl 40 hydrogenerated castor oil, methyl cellulose (MC), ethyl cellulose (EC), poloxamer, hydroxypropyl methylcellulose phthalate (HPMCP), poloxamer, hydrogenated castor and soybean oil, glyceryl palmitostearate, carnauba wax, polylactic acid (PLA), polyglycolic acid (PGA), a cellulose or cellulose derivative, cellulose acetate butyrate (CAB), colloidal silicon dioxide, a saccharide, glucose, polyvinyl acetate phthalate (PVAP), a wax, beeswax, hydrogel, gelatin, hydrogenated vegetable oil, polyvinyl acetal diethyl aminolactate (AEA), paraffin, shellac, sodium alginate, cellulose acetate phthalate (CAP), fatty oil, arabic gum, xanthan gum, glyceryl monostearate, octadecanoic acid, and a combination thereof.

In some embodiments, the intermediate material comprises a non-thermoplastic material. In some embodiments, the intermediate material is a non-thermoplastic material. In some embodiments, the non-thermoplastic material is selected from the group consisting of starch, pregelatinized starch, sodium starch glycolate (CMS-Na), sucrose, dextrin, lactose, microcrystalline cellulose (MCC), mannitol, magnesium stearate (MS), powdered silica gel, sodium alginate, titanium dioxide, glycerin, syrup, lecithin, soybean oil, tea oil, ethanol, propylene glycol, glycerol, Tween, animal fats, silicone oils, cacao butter, fatty acid glycerides, vaseline, chitosan, cetyl alcohol, stearyl alcohol, and a combination thereof.

In some embodiments, the intermediate material comprises a plasticizer. In some embodiments, the plasticizer comprises a block copolymer of polyoxyethylene-polyoxypropylene, vitamin e polyethylene glycol succinate, hydroxystearate, polyethylene glycol (such as PEG400), macrogol cetostearyl ether 12, polyoxyl 20 cetostearyl ether, polysorbate 20, polysorbate 60, polysorbate 80, acetin, acetylated triethyl citrate, tributyl citrate, tributyl o-acetylcitrate, triethyl citrate, polyoxyl 15 hydroxystearate, peg-40 hydrogenated castor oil, polyoxyl 35 castor oil, dibutyl sebacate, diethylphthalate, glycerine, methyl 4-hydroxybenzoate, glycerol, castor oil, oleic acid, tryacetin, or polyalkylene glycol.

In some embodiments, the method of designing a drug dosage form to provide a desired drug release profile comprises selecting an intermediate material not admixed with a drug. In some embodiments, the method of designing a drug dosage form to provide a desired drug release profile comprises selecting: (a) a first erodible material admixed with a drug; (b) a second material not admixed with a drug; and (c) an intermediate material not admixed with the drug. In some embodiments, the intermediate material not admixed with a drug is the same as a first erodible material admixed with the drug and/or a second material not admixed with the drug. In some embodiments, the intermediate material not admixed with a drug is different than a first erodible material admixed with the drug and/or a second material not admixed with the drug In some embodiments, the intermediate material not admixed with a drug is an erodible material. In some embodiments, the intermediate material not admixed with a drug is a material that erodes (e.g., completely erodes or undergoes complete dissolution) during the time a drug dosage form is in an individual.

In some embodiments, the method of designing a drug dosage form to provide a desired drug release profile comprises selecting an intermediate material not admixed with a drug, wherein the intermediate erodible material is selected based on a property of the intermediate erodible material. In some embodiments, selecting an intermediate material not admixed with a drug is based on the erosion rate of the intermediate erodible material. In some embodiments, selecting an intermediate material not admixed with a drug is based on a desired drug release profile of an oral dosage form. In some embodiments, selecting an intermediate material not admixed with a drug is based on a desired drug release profile of a drug dosage form, wherein thickness of the intermediate material may allow for control of the release rate of the drug from the drug dosage form, e.g., a pause or reduction in release of the drug from the drug dosage form. In some embodiments, thickness of a layer of an intermediate material is obtained based on Formula III.

E. Insulating Material

The present disclosure provides methods for designing a dosage form, such as an oral drug dosage form, to provide a desired release profile, such as a desired drug release profile, wherein the dosage form comprises a multi-layered structure comprising a plurality of layers of a first erodible material admixed with a compound (e.g., a drug), wherein the first erodible material is embedded in a second material not admixed with the compound (e.g., the drug), wherein the dosage form comprises an insulating material that is impermeable to bodily fluid, such as gastrointestinal fluid, and wherein the insulating material forms a barrier between the bodily fluid and a portion of the multilayer structure. In some embodiments, the second material is an insulating material. In some embodiments, the second material is not an insulating material. In some embodiments, the methods further comprise designing a drug dosage form with an intermediate material not admixed with a drug forms an intermediate layer between two or more layers of a first erodible material admixed with the drug.

In some embodiments, the insulating material forms a barrier between the bodily fluid, such as gastrointestinal fluid, and a portion of a layer of a first erodible material admixed with a drug. In some embodiments, the insulating material forms a barrier between the bodily fluid, such as gastrointestinal fluid, and a portion of a second material not admixed with a drug, wherein the second material is a second erodible material. In some embodiments, the insulating material forms a barrier between the bodily fluid, such as gastrointestinal fluid, and a portion of a multi-layered structure comprising a plurality of layers of a first erodible material admixed with a drug, wherein the first erodible material is embedded in a second material not admixed with the drug, wherein the second material is a second erodible material. In some embodiments, the insulating material forms a barrier between the bodily fluid, such as gastrointestinal fluid, and a portion of a multi-layered structure comprising a plurality of layers of a first erodible material admixed with a drug and an intermediate erodible material not admixed with the drug, wherein the first erodible material is embedded in a second material not admixed with the drug, and wherein the second material is a second erodible material.

In some embodiments, the insulating material comprises a thermoplastic material. In some embodiments, the insulating material is a thermoplastic material. In some embodiments, the insulating material is edible (i.e., suitable for consumption by an individual). In some embodiments, the insulating material is biocompatible (e.g., suitable for implantation). In some embodiments, the insulating material is selected from the group consisting of cellulose ethers, cellulose esters and acrylic resins. In some embodiments, the insulating material is selected from the group consisting of ethylcellulose, hydroxypropylmethylcellulose, hydroxypropyl cellulose, hydroxymethylcellulose, poly(meth)acrylic acid and derivatives thereof, such as the salts, amides or esters thereof are suitable for use as thermoplastic materials. In some embodiments, the insulating material is selected from the group consisting of mono- or diglycerides of C12-C30 fatty acids, C12-C30 fatty alcohols, waxes, and a combination thereof.

In some embodiments, the insulating material comprises a non-thermoplastic material. In some embodiments, the insulating material is a non-thermoplastic material. In some embodiments, the non-thermoplastic material is selected from the group consisting of ethyl cellulose (EC), polymethacrylate, non-toxic polyvinyl chloride, polyethylene, ethylene-vinyl acetate copolymer, silicone rubber, and a combination thereof.

In some embodiments, the insulating material is a non-erodible material. In some embodiments, the insulating material will not substantially erode for a period of at least about 36 hours after administration, such as at least about any of 42 hours, 48 hours, 54 hours, 60 hours, 66 hours, or 72 hours. In some embodiments, the insulating material is selected based on an erosion property of the insulating material, e.g., erosion at a specific pH.

Methods for Three-Dimensional Printing a Dosage Form

The present disclosure provides methods of printing a dosage form, such as a drug dosage form, formulated and configured to provide a desired release profile, such as a desired drug release profile, the methods comprising: dispensing a first erodible material admixed with a compound (e.g., a drug) and a second material not admixed with the compound (e.g., the drug) to produce a multi-layered structure comprising a plurality of layers of the first erodible material embedded in the second material, wherein each layer of the first erodible material has a pre-determined surface area, thickness, and mass fraction, such as drug mass fraction, wherein the pre-determined surface area, thickness, and/or mass fraction correlate with the desired release profile, and wherein upon exposure to the bodily fluid the drug is released in accordance with the desired drug release profile.

As used herein, "printing," "three-dimensional printing," "3D printing," "additive manufacturing," or equivalents thereof, refers to a process that produces three-dimensional objects, such as drug dosage forms, layer-by-layer using digital designs. The basic process of three-dimensional printing has been described in U.S. Pat. Nos. 5,204,055; 5,260,009; 5,340,656; 5,387,380; 5,503,785; and 5,633,021. Additional U.S. patents and patent applications that related to three-dimensional printing include: U.S. Pat. Nos. 5,490,962; 5,518,690; 5,869,170; 6,530,958; 6,280,771; 6,514,518; 6,471,992; 8,828,411; U.S. Publication Nos. 2002/0015728; 2002/0106412; 2003/0143268; 2003/0198677; 2004/0005360. The content of the above U.S. patents and patent applications is hereby incorporated by reference in their entirety.

In some embodiments, an additive manufacturing technique is used to produce the drug dosage forms described herein. In some embodiments, a layer-by-layer technique is used to produce the drug dosage forms described herein.

Different 3D printing methods have been developed for drug dosage form manufacturing in terms of raw materials, equipment, and solidification. These 3D printing methods include binder deposition (see Gibson et al., Additive Manufacturing Technologies: 3D Printing, Rapid Prototyping, and Direct Digital Manufacturing., 2 ed. Springer, New York, 2015; Katstra et al., Oral dosage forms fabricated by three dimensional printing, *J Control Release*, 66, 2000; Katstra et al., Fabrication of complex oral delivery forms by three dimensional printing, Dissertation in Materials Science and Engineering, Massachusetts Institute of Technology, 2001; Lipson et al., Fabricated: The New World of 3D printing, John Wiley & Sons, Inc., 2013; Jonathan, Karim 3D printing in pharmaceutics: a new tool for designing customized drug delivery systems, *Int J Pharm*, 499, 2016), material jetting (see Jonathan, Karim, 3D printing in pharmaceutics: a new tool for designing customized drug delivery systems, *Int J Pharm*, 499, 2016), extrusion (see Gibson et al., Additive Manufacturing Technologies: 3D Printing, Rapid Prototyping, and Direct Digital Manufacturing. 2 ed. Springer, New York, 2015), and photopolymerization (see Melchels et al., A review on stereolithography and its application in biomedical engineering. Biomaterials, 31, 2010).

In some embodiments, the drug dosage forms disclosed herein are 3D printed using an extrusion method. In some embodiments, the method of 3D printing comprises using a double screw extrusion method. In an extrusion process, material is extruded from robotically-actuated printing heads through printing nozzles. Unlike binder deposition, which requires a powder bed, extrusion methods can print on any substrate. A variety of materials can be extruded for three-dimensional printing, including thermoplastic materials disclosed herein, pastes and colloidal suspensions, silicones, and other semisolids. One common type of extrusion printing is fused deposition modeling, which uses solid polymeric filaments for printing. In fused deposition modeling, a gear system drives the filament into a heated nozzle assembly for extrusion (see Gibson et al., Additive Manufacturing Technologies: 3D Printing, Rapid Prototyping, and Direct Digital Manufacturing, 2 ed. Springer, New York, 2015).

In some embodiments, the 3D printing methods disclosed herein comprise a continuous feed method.

In some embodiments, the 3D printing methods disclosed herein comprise a batch feed method.

The method instructions for 3D printing a drug dosage form disclosed herein may be generated a variety of ways, including direct coding, derivation from a solid CAD model, or other means specific to the 3D printing machine's computer interface and application software. These instructions may include information on the number and spatial placement of droplets, and on general 3D print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the print parameters, and the material properties.

Because 3D printing may handle a range of pharmaceutical materials and control both composition and architecture locally, 3D printing is well suited to the fabrication of drug dosage forms with complex geometry and composition in accordance with the present invention.

Manufacturing the drug dosage forms using 3D printing methods also facilitates personalized medicine. Personalized medicine refers to stratification of patient populations based on biomarkers to aid therapeutic decisions and personalized dosage form design. Modifying digital designs is easier than modifying physical equipment. Also, automated, small-scale three-dimensional printing may have negligible operating cost. Hence, 3D printing can make multiple small, individualized batches economically feasible and enable personalized dosage forms designed to improve adherence.

Personalized drug dosage forms allow for tailoring the amount of drug delivered based on a patient's mass and metabolism. 3D printed dosage forms could ensure accurate dosing in growing children and permit personalized dosing of highly potent drugs. Personalized dosage forms can also combine all of patients' medications into a single daily dose, thus improve patients' adherence to medication and treatment compliance.

The drug dosage forms disclosed in the present application can be printed on a commercial scale. For example, in some embodiments, the methods disclosed herein may be used to 3D print 10,000 to 100,000 tablets of a drug dosage form per hour. In some embodiments, the methods disclosed herein may be used to 3D print 10,000 to 100,000 drug dosage forms per hour.

In some embodiments, the method for 3D printing of a drug dosage form formulated to provide a desired drug release profile comprises dispensing a first erodible material admixed with a drug and a second material not admixed with the drug to produce a multi-layered structure comprising a plurality of layers of the first erodible material embedded in the second material. In some embodiments, each printed layer of a first erodible material admixed with a drug has a pre-determined surface area, thickness, and drug mass fraction, wherein the pre-determined surface area, thickness, and/or drug mass fraction correlate with a desired drug release profile, and wherein upon exposure to the bodily fluid, such as gastrointestinal fluid, the drug is released in accordance with the desired drug release profile.

In some embodiments, the surface areas of a first erodible material in at least two of the layers are different from each other. In some embodiments, the surface areas of a first erodible material in at least two of the layers are the same as each other.

In some embodiments, the thicknesses of each of a plurality of layers of a first erodible material are the same. In some embodiments, the thickness of at least two layers of a first erodible material are different from each other.

In some embodiments, the drug mass fraction in each of a plurality of layers of a first erodible material are the same. In some embodiments, the drug mass fractions in at least two layers of a first erodible materials are different from each other.

In some embodiments, the second material is a second erodible material. In some embodiments, the first erodible material and a second erodible material are different from each other. In some embodiments, the first erodible material and a second erodible material are the same.

In some embodiments, the second material is an insulating material that is impermeable to bodily fluid, such as gastrointestinal fluid, wherein the insulating material forms a barrier between the bodily fluid and a portion of the multi-layered structure. In some embodiments, the insulating material is non-erodible.

In some embodiments, the methods for 3D printing of a drug dosage form formulated and configured to provide a desired drug release profile further comprise dispensing an insulating material that is impermeable to bodily fluid, such as gastrointestinal fluid, wherein the insulating material forms a barrier between the bodily fluid and a portion of the multi-layered structure.

In some embodiments, the first erodible material and a second material are dispensed by different printing heads.

In some embodiments, the first erodible material, a second material, and an insulating material are dispensed by different printing heads.

In some embodiments, the 3D printing is carried out by fused deposition modeling (FDM). In some embodiments, the 3D printing is carried out by non-filament FDM. In some embodiments, the 3D printing is carried out by inkjet printing. In some embodiments, the 3D printing is carried out by selective laser sintering (SLS). In some embodiments, the 3D printing is carried out by stereolithography (SLA or SL). In some embodiments, the 3D printing is carried out by PolyJet, Multi-Jet Printing System (MJP), Perfactory, Solid Object Ultraviolet-Laser Printer, Bioplotter, 3D Bioprinting, Rapid Freeze Prototyping, Fused Deposition Modelling (FDM), Benchtop System, Selective Deposition Lamination (SDL), Laminated Objet Manufacutring (LOM), Ultrasonic Consolidation, ColorJet Printing (CJP), EOSINT Systems, Laser Engineered Net Shaping (LENS) and Aerosol Jet System, Electron Beam Melting (EBM), Laser CUSING®, Selective Laser Melting (SLM), Phenix PXTM Series, Microsintering, Digital Part Materialization (DPM), or VX System.

In some embodiments, the three-dimensional printing is carried out by hot melt extrusion coupled with a three-dimensional printing technique, such as FDM.

In some embodiments, the first erodible material and a second material, wherein the second material is a second erodible material, have the same erosion rate.

In some embodiments, the thickness of each layer is no more than about 22 mm, such as no more than about any of 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, or 0.01 mm. In some embodiments, the thickness of a layer is no more than about 22 mm, such as no more than about any of 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, or 0.01 mm. In some embodiments, the thickness of a layer is about any of 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, or 0.01 mm.

In some embodiments, the methods for 3D printing of a drug dosage form formulated and configured to provide a desired drug release profile further comprise dispensing an intermediate material not admixed with the drug, wherein the intermediate material forms an intermediate layer between two or more layers of the first erodible material. In some embodiments, the intermediate material is the same as a first erodible material and/or a second material. In some embodiments, the intermediate material is different than a first erodible material and/or a second material.

In some embodiments, the methods for 3D printing of a drug dosage form formulated and configured to provide a desired drug release profile further comprise dispensing an intermediate material not admixed with the drug, wherein the intermediate material forms an intermediate layer between two or more layers of the first erodible material. In some embodiments, the intermediate material is the same as a first erodible material and/or a second material.

In some embodiments, the drug dosage forms 3D printed by the methods disclosed herein further comprises a second drug. In some embodiments, the second drug is admixed with a first erodible material. In some embodiments, the second drug is admixed with an insulating material, wherein the second drug is released from the insulating material.

In some embodiments, the methods for 3D printing of a drug dosage form formulated and configured to provide a desired drug release profile further comprise dispensing a third erodible material admixed with a second drug, wherein a multi-layered structure further comprises a plurality of layers of the third erodible material embedded in a second material. In some embodiments, each layer of a third erodible material has a pre-determined surface area, thickness, and drug mass fraction, wherein the pre-determined surface area, thickness, and/or drug mass fraction correlate with a second desired drug release profile, and wherein upon exposure to bodily fluid, such as gastrointestinal fluid, the second drug is released in accordance with the second desired drug release profile. In some embodiments, the third erodible material is the same as a first erodible material and/or second material.

In some embodiments, the erosion of a first erodible material is pH dependent.

In some embodiments, the erosion of a third erodible material is pH dependent.

The 3D printing methods of the present disclosure encompass printing the materials in any order that will allow for production of a drug dosage form disclosed herein. In some embodiments, the method for three-dimensional printing of a drug dosage form comprises dispensing an insulating material to form a structure of a specific thickness, wherein the multi-layered structure is dispensed into the structure of the insulating material. In some embodiments, the method for three-dimensional printing of a drug dosage form further comprises dispensing an insulating material to form a structure of a specific thickness on top of a previously dispensed structure of the insulating material. In some embodiments, the method for three-dimensional printing of a drug dosage form comprises dispensing an insulating material after dispensing of a first erodible material and/or a second material.

In some embodiments, the method for three-dimensional printing of a drug dosage form comprises dispensing a first erodible material and dispensing a second material, wherein the first erodible material and the second material are dispensed by different printing heads. In some embodiments, the method for three-dimensional printing of a drug dosage form comprises dispensing a first erodible material, dispensing a second material, and dispensing an insulating material, wherein the first erodible material, the second material, and the insulating material are dispensed by different printing heads.

In some embodiments, the method for three-dimensional printing of a drug dosage form comprises designing the drug dosage form, in whole or in part, on a computer system. In some embodiments, the method comprises inputting parameters of the desired drug release profile and/or a drug dosage form into the computer system. In some embodiments, the method comprises providing one or more parameters of the drug dosage form, e.g., layer surface area, thickness, drug mass fraction; erosion rate. In some embodiments, the method comprises providing the desired drug release profile. In some embodiments, the methods comprise creating a virtual image of a drug dosage form. In some embodiments, the method comprises creating a computer model that contains the pre-determined parameters. In some embodiments, the method comprises feeding the pre-determined parameters to a three-dimensional printer and printing a drug dosage form according to such pre-determined parameters. In some embodiments, the method comprises creating a three-dimensional drawing of a drug dosage form based on the pre-determined parameters of the drug dosage form, wherein the three-dimensional drawing is created on a computer system. In some embodiments, the method comprises converting, such as slicing, a three-dimensional drawing of a drug dosage form into three-dimensional printing code, e.g., G code. In some embodiments, the method comprises using the computer system to execute three-dimensional printing code, thereby printing a drug dosage form described herein.

In some embodiments, there is provided a method for three-dimensional printing (e.g., 3D printing by FDM, for example non-filament FDM) of an oral drug dosage form formulated and configured to provide a desired drug release profile, wherein the drug dosage form comprises a multi-layered structure comprising a plurality of layers of a first erodible material admixed with a drug having a pre-determined drug mass faction ($m_F$), wherein the first erodible material is embedded in a second material not admixed with the drug, the method comprising: (a) dividing the desired drug release profile into a plurality of time intervals ($t_n$), each time interval corresponding to a layer in the multi-layered structure; (b) determining (or calculating) the percentage of drugs to be released during each time interval ($\%_L$); (c) determining (or calculating) the thickness of each layer ($H_n$) of the multi-layered structure based on the erosion rate of the first erodible material (V), wherein $H_n = t_n * V$; (d) determining (or calculating) the surface area of each layer based on $\%_L$, $H_n$, $m_F$, total amount of drug in the oral drug dosage form ($m_{DTot}$), and the density of the first erodible material ($\rho$), wherein:

$$S_n = \frac{\%_L * m_{DTot}}{\rho * Hn * m_F}$$

(e) dispensing (or depositing) the first erodible material admixed with the drug based on the determined $H_n$ and $S_n$ for each layer, thereby printing the multi-layered structure; and (f) before, after, or during step (e), dispensing the second material not admixed with the drug. In some embodiments, the release profile of the oral drug dosage form is equivalent to the desired release profile based on Chow's method or similarity factor calculation method. In some embodiments, the method further comprises creating a virtual image of the drug dosage form prior to the dispending steps. In some embodiments, the method further comprises creating a computer model that contains the pre-determined parameters prior to the dispensing step. In some embodiments, the method further comprises feeding the pre-determined parameters to the three-dimensional printer prior to the dispensing step.

In some embodiments, a top layer is printed at the top of the multi-layered structure. The top layer can be printed before or after the multi-layered structure. For example, in some embodiments, there is provided a method for three-dimensional printing (e.g., 3D printing by FDM, for example non-filament FDM) of an oral drug dosage form formulated and configured to provide a desired drug release profile, wherein the drug dosage form comprises a multi-layered structure comprising a plurality of layers of a first erodible material admixed with a drug having a pre-determined drug mass faction ($m_F$), wherein the first erodible material is embedded in a second material not admixed with the drug, the method comprising: (a) dividing the desired drug release profile into a plurality of time intervals ($t_n$), each time interval corresponding to a layer in the multi-layered structure; (b) determining (or calculating) the percentage of drugs to be released during each time interval ($\%_L$); (c) determining (or calculating) the thickness of each layer ($H_n$) of the multi-layered structure based on the erosion rate of the first erodible material (V), wherein $H_n = t_n * V$; (d) determining (or calculating) the surface area of each layer based on %$_L$, H$_n$, m$_F$, total amount of drug in the oral drug dosage form (m$_{DTot}$), and the density of the first erodible material (ρ), wherein:

$$S_n = \frac{\%_L * m_{DTot}}{\rho * Hn * m_F}$$

(e) dispensing (or disposing) the first erodible material admixed with the drug based on the determined H$_n$ and S$_n$ for each layer, thereby printing the multi-layered structure; (f) dispensing (or depositing) a top erodible material not admixed with the drug on top of the multi-layered structure to form a top layer, wherein the surface area of the top layer is the same or larger than the first layer of the multi-layered structure immediately underneath the top layer; and (g) before, after, or during step (e), dispensing the second material not admixed with the drug. In some embodiments, the thickness of the top layer is determined based on the delay time needed for the drug release from the multi-layered structure. In some embodiments, the top erodible material is the same as the first erodible material. In some embodiments, the top erodible material is different from the first erodible material. In some embodiments, the release profile of the oral drug dosage form is equivalent to the desired release profile based on Chow's method or similarity factor calculation method. In some embodiments, the method further comprises creating a virtual image of the drug dosage form prior to the dispending steps. In some embodiments, the method further comprises creating a computer model that contains the pre-determined parameters prior to the dispensing step. In some embodiments, the method further comprises feeding the pre-determined parameters to the three-dimensional printer prior to the dispensing step.

In some embodiments, the method further comprises dispending dispensing an insulating material that is impermeable to bodily fluid, wherein the insulating material forms a barrier between the bodily fluid and at least a portion of the multi-layered structure. In some embodiments, the method further comprises dispensing an intermediate material not admixed with the drug, wherein the intermediate material forms one or more intermediate layers between two or more layers of the first erodible material.

In some embodiments, there is provided a method for three-dimensional printing (e.g., 3D printing by FDM, for example non-filament FDM) of an oral drug dosage form formulated and configured to provide a desired drug release profile, wherein the drug dosage form comprises a multi-layered structure comprising a plurality of layers of a first erodible material admixed with a drug having a pre-determined drug mass faction (mF), wherein the first erodible material is embedded in a second material not admixed with the drug, the method comprising: (a) dividing the desired drug release profile into a plurality of time intervals (tn), each time interval corresponding to a layer in the multi-layered structure; (b) determining (or calculating) the percentage of drugs to be released during each time interval (% L); (c) determining (or calculating) the thickness of each layer (Hn) of the multi-layered structure based on the erosion rate of the first erodible material (V), wherein Hn=tn*V; (d) determining (or calculating) the surface area of each layer based on % L, Hn, mF, total amount of drug in the oral drug dosage form (mDTot), and the density of the first erodible material (ρ), wherein:

$$S_n = \frac{\%_L * m_{DTot}}{\rho * Hn * m_F}$$

(e) dispensing (or disposing) the first erodible material admixed with the drug based on the determined H$_n$ and S$_n$ for each layer, thereby printing the multi-layered structure; (f) dispensing (or depositing) a top erodible material not admixed with the drug on top of the multi-layered structure to form a top layer, wherein the surface area of the top layer is the same or larger than the first layer of the multi-layered structure immediately underneath the top layer; (g) before, after, or during step (e), dispensing the second material not admixed with the drug; (h) determining the drug release profile of the oral drug dosage form produced by steps (a)-(g); (i) comparing the drug release profile of the oral drug dosage form with the desired drug release profile; (j) adjusting one or more parameters selected from: the first erodible material, the second material, the surface area of the one or more of the layers of the first erodible material, the thickness of one or more layers of the first erodible material, and the mass fraction of the drug in one or more layers of the first erodible material; and (k) three-dimensional printing a second oral drug dosage form based on the adjusted parameters. In some embodiments, the release profile of the oral drug dosage form is equivalent to the desired release profile based on Chow's method or similarity factor calculation method. In some embodiments, the method further comprises creating a virtual image of the drug dosage form prior to the dispending steps. In some embodiments, the method further comprises creating a computer model that contains the pre-determined parameters prior to the dispensing step. In some embodiments, the method further comprises feeding the pre-determined parameters to the three-dimensional printer prior to the dispensing step.

In some embodiments, there is provided a method for three-dimensional printing (e.g., 3D printing by FDM, for example non-filament FDM) of an oral drug dosage form formulated and configured to provide a desired drug release profile, wherein the drug dosage form comprises a multi-layered structure comprising a plurality of layers of a first erodible material admixed with a drug having a pre-determined drug mass faction (mF), wherein the first erodible material is embedded in a second material not admixed with the drug, the method comprising: (a) determining the drug release profile of an original oral drug dosage form; (b) comparing the drug release profile of the oral drug dosage form with the desired drug release profile; (c) adjusting one or more parameters selected from: the first erodible material, the second material, the surface area of the one or more of the layers of the first erodible material, the thickness of one or more layers of the first erodible material, and the mass fraction of the drug in one or more layers of the first erodible material; and (d) three-dimensional printing of the oral drug dosage form based on the adjusted parameters. In some embodiments, the release profile of the oral drug dosage form is equivalent to the desired release profile based on Chow's method or similarity factor calculation method. In some embodiments, the method further comprises creating a virtual image of the drug dosage form prior to the dispending steps. In some embodiments, the method further comprises creating a computer model that contains the pre-determined parameters prior to the dispensing step. In some embodiments, the method further comprises feeding the pre-determined parameters to the three-dimensional printer prior to the dispensing step.

In some embodiments, there is provided a method for three-dimensional printing (e.g., 3D printing by FDM, for example non-filament FDM) of an oral drug dosage form formulated and configured to provide a desired drug release profile, wherein the drug dosage form comprises a multi-layered structure comprising a plurality of layers of a first erodible material admixed with a drug having a pre-determined thickness and a predetermined surface area, wherein the first erodible material is embedded in a second material not admixed with the drug, wherein the surface area of each of the plurality of layers of the first erodible material in the multi-layered structure decreases sequentially from the surface to the interior of the oral dosage form, wherein when the oral dosage form is exposed to a bodily fluid the plurality of layers are exposed to the bodily fluid in a sequential pattern, with the layer with the largest surface area exposed to the bodily fluid first, the method comprising: (a) dispensing (or depositing) the first erodible material admixed with the drug based on the determined $H_n$ and $S_n$ for each layer, thereby printing the multi-layered structure; and (b) before, after, or during step (a), dispensing the second material not admixed with the drug. In some embodiments, the method further comprises dispensing a top erodible material not admixed with the drug on top of the multi-layered structure to form a top layer, wherein the surface area of the top layer is the same or larger than the first layer of the multi-layered structure immediately underneath the top layer. In some embodiments, the thickness of the top layer is determined based on the delay time needed for the drug release from the multi-layered structure. In some embodiments, the method further comprises creating a computer model that contains the pre-determined parameters prior to the dispensing step. In some embodiments, the method further comprises feeding the pre-determined parameters to the three-dimensional printer prior to the dispensing step.

In some embodiments, the oral drug dosage form comprises two or more multi-layered structures, and optionally each of the multi-layered structure is produced sequentially or simultaneously by any of the methods described herein. Thus, for example, in some embodiments, there is provided a method for three-dimensional printing of an oral drug dosage form formulated and configured to provide a first desired drug release profile and a second desired drug release profile, wherein the drug dosage form comprises a first multi-layered structure comprising a plurality of layers of a first erodible material admixed with a drug having a pre-determined drug mass faction ($m_F$), wherein the first erodible material is embedded in a second material not admixed with a first drug, and a second multi-layered structure comprising a plurality of layers of a third erodible material admixed with a fourth drug having a pre-determined drug mass faction, wherein the third erodible material is embedded in a fourth material not admixed with the drug, the method comprising: (a) dividing each of the desired drug release profile into a plurality of time intervals ($t_n$), each time interval corresponding to a layer in a corresponding multi-layered structure; (b) calculating the percentage of drugs to be released during each time interval ($\%_L$); (c) calculating the thickness of each layer ($H_n$) of the multi-layered structures based on the erosion rate of the first erodible material or third erodible material (V), wherein $H_n=t_n*V$; (d) calculating the surface area of each layer based on $\%_L$, $H_n$, $m_F$, total amount of drug in the oral drug dosage form ($m_{DTot}$), and the density of the first or first erodible material ($\rho$), wherein:

$$S_n = \frac{\%_L * m_{DTot}}{\rho * Hn * m_F}$$

(e) dispensing the first erodible material admixed with the first drug and third erodible material admixed with the second drug based on the determined $H_n$ and $S_n$ for each layer, thereby printing the two multi-layered structures; (f) before, after, or during step (e), dispensing the second material and fourth material not admixed with the drug. In some embodiments, the first erodible material and the third erodible material are the same. In some embodiments, the second and fourth materials are the same. In some embodiments, the first drug and the second drug are the same. In some embodiments, the first drug and the second drug are different.

Dosage Forms

The present application also provides any of the dosage claim produced by the 3D printing methods described herein. The present disclosure provides, using any of the methods for designing or methods of 3D printing disclosed herein, a dosage form, such as a drug dosage form or a reagent dosage form, to provide a desired release profile, such as a desired drug release profile, wherein the dosage form comprises a multi-layered structure comprising a plurality of layers of a first erodible material admixed with the compound (e.g., the drug), wherein the first erodible material is embedded in a second material not admixed with the compound (e.g., the drug). In some embodiments, the materials of a drug dosage form, e.g., a first erodible material admixed with a drug, a second material not admixed with the drug, an intermediate material, an insulating material, are integrated (e.g., do not form components that may be readily separated).

In some embodiments, the plurality of layers of a first erodible material is between about 5 layers to about 2500 layers, such as between any of about 10 layers to about 2500 layers, about 25 layers to about 100 layers, about 50 layers to about 200 layers, about 100 layers to about 200 layers, about 150 layers to about 250 layers, about 200 layers to about 250 layers, about 500 layers to about 1000 layers, or about 2000 layers to about 2400 layers.

In some embodiments, the surface areas of a first erodible material in at least two of the layers are different from each other. In some embodiments, the surface areas of a first erodible material in at least two of the layers are the same as each other.

In some embodiments, the thicknesses of each of a plurality of layers of a first erodible material are the same. In some embodiments, the thickness of at least two layers of a first erodible material are different from each other.

In some embodiments, the drug mass fraction in each of a plurality of layers of a first erodible material are the same. In some embodiments, the drug mass fractions in at least two layers of a first erodible materials are different from each other.

In some embodiments, the second material is a second erodible material. In some embodiments, the first erodible material and a second erodible material are different from each other. In some embodiments, the first erodible material and a second erodible material are the same.

In some embodiments, the second material is an insulating material that is impermeable to bodily fluid, such as gastrointestinal fluid, wherein the insulating material forms a barrier between the bodily fluid and a portion of the multi-layered structure. In some embodiments, the insulating material is non-erodible.

In some embodiments, the drug dosage form further comprises an insulating material that is impermeable to bodily fluid, such as gastrointestinal fluid, wherein the insulating material forms a barrier between the bodily fluid and a portion of the multi-layered structure.

In some embodiments, the first erodible material and a second material, wherein the second material is a second erodible material, have the same erosion rate.

In some embodiments, the thickness of each layer is no more than about 22 mm, such as no more than about any of 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, or 0.01 mm. In some embodiments, the thickness of a layer is no more than about 22 mm, such as no more than about any of 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, or 0.01 mm. In some embodiments, the thickness of a layer is about any of 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, or 0.01 mm.

In some embodiments, the drug dosage form further comprises an intermediate material not admixed with the drug, wherein the intermediate material forms an intermediate layer between two or more layers of the first erodible material. In some embodiments, the intermediate material is the same as a first erodible material and/or a second material. In some embodiments, the intermediate material is different than a first erodible material and/or a second material.

The drug dosage forms described herein may comprise any number of drugs. In some embodiments, the drug dosage forms comprise two or more drugs, such as any of 3, 4, 5, 6, 7, 8, 9 or 10 drugs. In some embodiments, the drug dosage forms further comprise a second drug. In some embodiments, the second drug is admixed with a first erodible material. In some embodiments, the second drug is admixed with an insulating material, wherein the second drug is released from the insulating material.

In some embodiments, the drug dosage form further comprises a third erodible material admixed with a second drug, wherein a multi-layered structure further comprises a plurality of layers of the third erodible material embedded in a second material. In some embodiments, each layer of a third erodible material has a pre-determined surface area, thickness, and drug mass fraction, wherein the pre-determined surface area, thickness, and/or drug mass fraction correlate with a second desired drug release profile, and wherein upon exposure to bodily fluid, such as gastrointestinal fluid, the second drug is released in accordance with the second desired drug release profile. In some embodiments, the third erodible material is the same as a first erodible material and/or second material.

In some embodiments, the erosion of an erodible material is pH dependent. In some embodiments, the erosion of a first erodible material is pH dependent. In some embodiments, the erosion of a second erodible material is pH dependent. In some embodiments, the erosion of a third erodible material is pH dependent. In some embodiments, the erosion of an intermediate material is pH dependent. In some embodiments, the erosion of an erodible material occurs above a pH of about 5.5 to about 7. In some embodiments, the erosion of an erodible material occurs above a pH of about 5.5, about 6, about 6.5, or about 7. In some embodiments, the erodible material is an enteric coating.

In some embodiments, the dosage form, such as an oral drug dosage form, is coated, such as embedded, encased, or attached thereto, with a film or a coating, e.g., sugar coating or gelatin layer.

In some embodiments, the total mass of drugs in a drug dosage form is between about 1500 mg to about 0.01 mg. In some embodiments, the total mass of drugs in a drug dosage form is less than about 1500 mg, such as less than about any of 1400 mg, 1300 mg, 1200 mg, 1100 mg, 1000 mg, 900 mg, 800 mg, 700 mg, 600 mg, 500 mg, 450 mg, 400 mg, 350 mg, 300 mg, 250 mg, 200 mg, 150 mg, 100 mg, 75 mg, 50 mg, 45 mg, 40 mg, 35 mg, 30 mg, 25 mg, 20 mg, 15 mg, 10 mg, 5 mg, 4 mg, 3 mg, 2 mg, 1 mg, 0.75 mg, 0.5 mg, 0.25 mg, or 0.1 mg. In some embodiments, the total mass of drugs in a drug dosage form is about 1500 mg, such as about any of 1400 mg, 1300 mg, 1200 mg, 1100 mg, 1000 mg, 900 mg, 800 mg, 700 mg, 600 mg, 500 mg, 450 mg, 400 mg, 350 mg, 300 mg, 250 mg, 200 mg, 150 mg, 100 mg, 75 mg, 50 mg, 45 mg, 40 mg, 35 mg, 30 mg, 25 mg, 20 mg, 15 mg, 10 mg, 5 mg, 4 mg, 3 mg, 2 mg, 1 mg, 0.75 mg, 0.5 mg, 0.25 mg, or 0.1 mg.

In some embodiments, the mass of a drug in a drug dosage form is between about 1500 mg to about 0.01 mg. In some embodiments, the mass of a drug in a drug dosage form is less than about 1500 mg, such as less than about any of 1400 mg, 1300 mg, 1200 mg, 1100 mg, 1000 mg, 900 mg, 800 mg, 700 mg, 600 mg, 500 mg, 450 mg, 400 mg, 350 mg, 300 mg, 250 mg, 200 mg, 150 mg, 100 mg, 75 mg, 50 mg, 45 mg, 40 mg, 35 mg, 30 mg, 25 mg, 20 mg, 15 mg, 10 mg, 5 mg, 4 mg, 3 mg, 2 mg, 1 mg, 0.75 mg, 0.5 mg, 0.25 mg, or 0.1 mg. In some embodiments, the mass of a drug in a drug dosage form is about 1500 mg, such as about any of 1400 mg, 1300 mg, 1200 mg, 1100 mg, 1000 mg, 900 mg, 800 mg, 700 mg, 600 mg, 500 mg, 450 mg, 400 mg, 350 mg, 300 mg, 250 mg, 200 mg, 150 mg, 100 mg, 75 mg, 50 mg, 45 mg, 40 mg, 35 mg, 30 mg, 25 mg, 20 mg, 15 mg, 10 mg, 5 mg, 4 mg, 3 mg, 2 mg, 1 mg, 0.75 mg, 0.5 mg, 0.25 mg, or 0.1 mg.

In some embodiments, the materials of the drug dosage forms described herein, including a first erodible material, a second material, a second erodible material, an intermediate material, an intermediate erodible material, and an insulating material, further comprise another agent. In some embodiments, the other agent is an excipient. In some embodiments, the other agent is a bulking agent. In some embodiments, the other agent is a light shielding agent, such as an opacifier.

In some embodiments, the drug dosage form is suitable for oral administration. The drug dosage forms of the present invention can be, for example, any size, shape, or weight that is suitable for oral administration to specific patients, such as children and adults. In some embodiments, the drug dosage form is suitable for oral administration to an individual, wherein selection of size, shape, or weight of the drug dosage form is based on an attribute of the individual. In some embodiments, the attribute of the individual is one or more of height, weight, or age.

In some embodiments, the drug dosage form has a dimension that is less than about 22 mm, such as less than about 21 mm, less than about 20 mm, less than about 19 mm, less than about 18 mm, less than about 17 mm, less than about 16 mm, less than about 15 mm, less than about 14 mm, less than about 13 mm, less than about 12 mm, less than about 11 mm, less than about 10 mm, less than about 9 mm, less than about 8 mm, less than about 7 mm, less than about 6 mm, less than about 5 mm, less than about 4 mm, less than about 3 mm, less than about 2 mm, or less than about 1 mm. In some embodiments, the drug dosage form has a dimension that is about 1 mm to about 22 mm, such as about 21 mm, about 20 mm, about 19 mm, about 18 mm, about 17 mm, about 16 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, or about 2 mm.

In some embodiments, the drug dosage form is of a suitable size and shape for its intended use, e.g., implantation.

In some embodiments, the drug dosage form has a total weight of about 50-600 mg, such as about any of 50-100, 100-150, 150-200, 200-250, 250-300, 300-350, 350-400, 400-450, 450-500, 500-550, or 550-600 mg. In some embodiments, the drug dosage form has a total weight of about 50-400 mg. In some embodiments, the drug dosage form has a total weight of about 75-300 mg. In some embodiments, the drug dosage form has a total weight of about 100-200 mg. In some embodiments, the drug dosage form has a total weight of less than about 600 mg, 550 mg, 500 mg, 450 mg, 400 mg, 350 mg, 300 mg, 250 mg, 200 mg, 150 mg, 100 mg, 75 mg, or 50 mg.

FIG. 2B shows an exemplary drug dosage form 240 formulated and configured to provide a desired drug release profile comprising a multi-layered structure comprising a plurality of layers of a first erodible material admixed with a drug 255, wherein the first erodible material is embedded in a second material not admixed with the drug 250. The exemplary drug dosage form 240 further comprises an insulating material 245 around all surfaces except the top surface. The direction of erosion of the first erodible material admixed with a drug is indicated by an arrow 260. Optionally, the second material not admixed with the drug 250 is a second erodible material.

FIG. 2C shows an exemplary drug dosage form 265 formulated and configured to provide a desired drug release profile comprising a multi-layered structure comprising a plurality of layers of a first erodible material admixed with a drug 280, wherein the first erodible material is embedded in a second material not admixed with the drug 275. The exemplary drug dosage form 265 further comprises an insulating material 270 around all surfaces except the top surface. The direction of erosion of the first erodible material admixed with a drug is indicated by an arrow 285. Optionally, the second material not admixed with the drug 275 is a second erodible material.

FIG. 3A shows an exemplary drug dosage form 300 formulated and configured to provide a desired drug release profile comprising a multi-layered structure comprising a plurality of layers of a first erodible material admixed with a drug 315, wherein the first erodible material is embedded in a second material not admixed with the drug 305 (pictured as a translucent material to allow for visualization of other components). The exemplary drug dosage form 300 further comprises an insulating material 305 around all surfaces except the top surface. The direction of erosion of the first erodible material admixed with a drug is indicated by an arrow 320. Optionally, the second material not admixed with the drug 305 is a second erodible material.

FIG. 4C shows an exemplary drug dosage form 425 formulated and configured to provide a desired drug release profile comprising a plurality of multi-layered structures comprising a plurality of layers of a first erodible material admixed with a drug 428, 433, 441 wherein the first erodible material is embedded in a second material not admixed with the drug 429. The exemplary drug dosage form 430 further comprises an insulating material 430 that serves to control the exposure of each multi-layered structure comprising a plurality of layers of the first erodible material admixed with the drug to bodily fluid, such as gastrointestinal fluid (see also FIG. 4B). Optionally, the second material not admixed with the drug 429 is a second erodible material.

Figure 5:
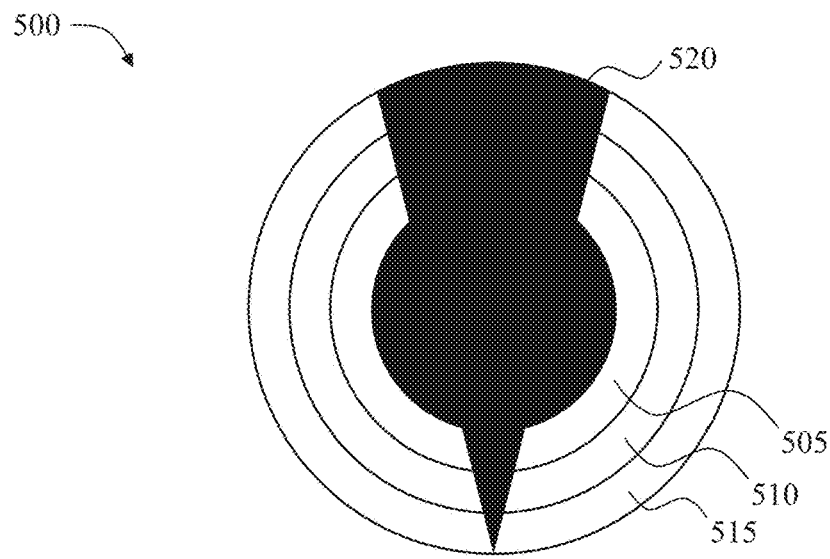
FIG. 5 shows a cross-sectional view of an exemplary drug dosage form 500 formulated and configured to provide a desired drug release profile.

FIG. 5 shows a cross-sectional view of an exemplary drug dosage form 500 formulated and configured to provide a desired drug release profile comprising a multi-layered structure comprising a plurality of layers of a first erodible material admixed with a drug 505, 510, 515, wherein the first erodible material is embedded in a second material not admixed with the drug 520. Optionally, the second material not admixed with the drug 520 is a second erodible material.

Figure 6:
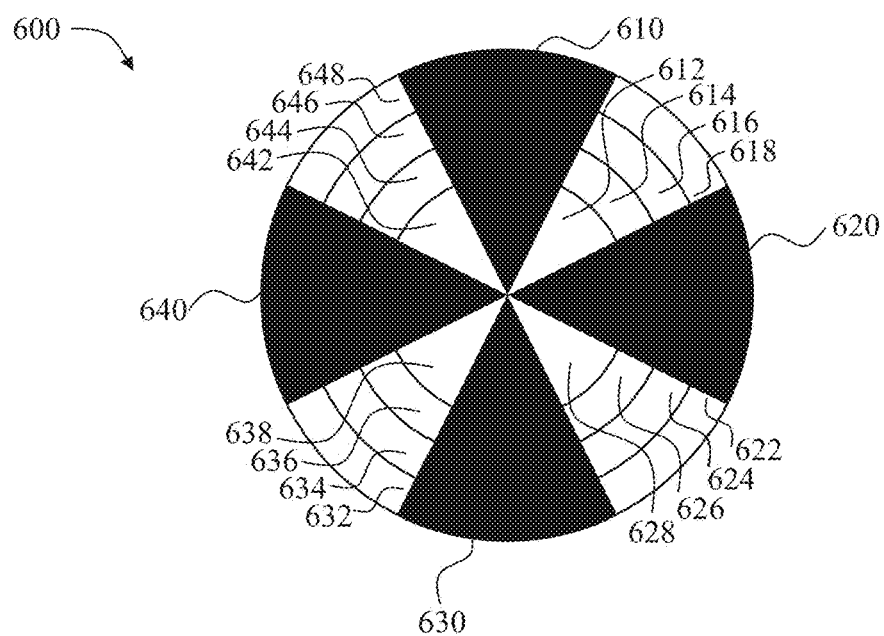
FIG. 6 shows a cross-sectional view of an exemplary drug dosage form 600 formulated and configured to provide a desired drug release profile.

FIG. 6 shows a cross-sectional view of an exemplary drug dosage form 600 formulated and configured to provide a desired drug release profile comprising a multi-layered structure comprising a plurality of layers of a first erodible material admixed with a drug 612-618, 622-628, 632-638, 642-648, wherein the first erodible material is embedded in a second material not admixed with the drug 610, 620, 630, 640. Optionally, one or more of the second material not admixed with the drug 610, 620, 630, 640 is a second erodible material.

Figure 8B:
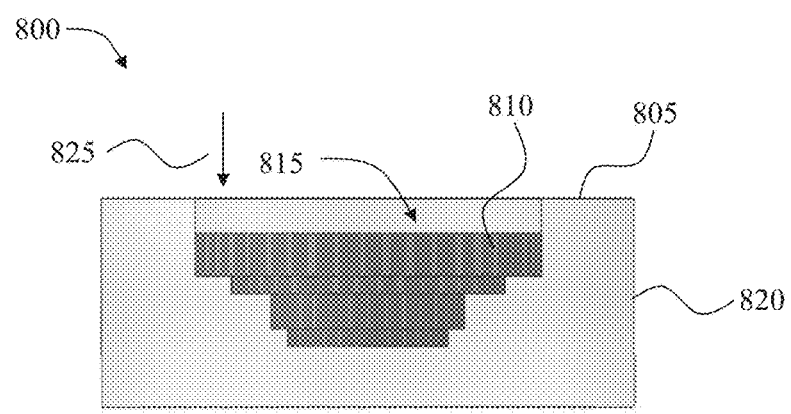

FIG. 8A shows an exemplary drug dosage form 800 formulated and configured to provide a desired drug release profile comprising a multi-layered structure comprising a plurality of layers of a first erodible material admixed with a drug 810, wherein the first erodible material is embedded in a second material not admixed with the drug 820 (pictured as a translucent material to allow for visualization of other components). The drug dosage form 800 comprises a rim formed from the second material not admixed with the drug 805, wherein the rim forms a space 815 on top of the multi-layered structure (FIG. 8A). A cross-sectional view of the drug dosage form 800 is illustrated in FIG. 8B. The direction of erosion of the first erodible material admixed with the drug 810 is indicated by an arrow 830 (FIG. 8B).

Figure 9A:
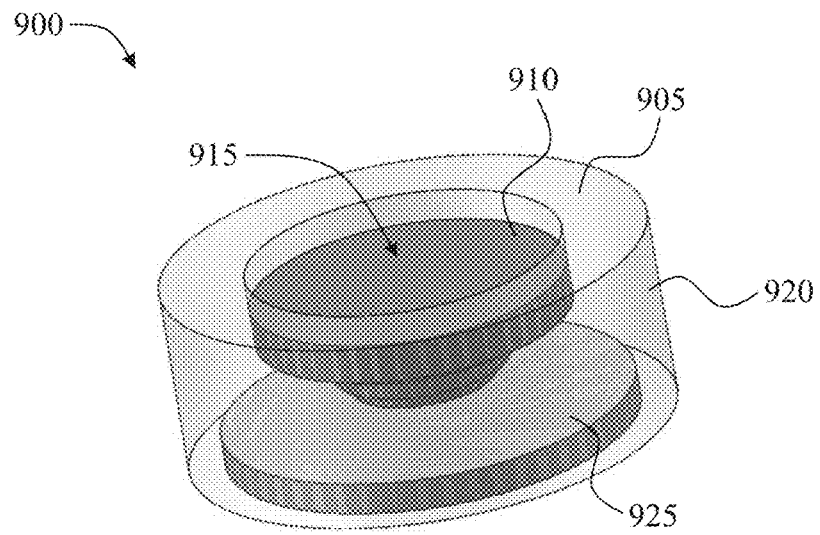
FIGS. 9A-9B show an exemplary drug dosage form 900.
Figure 9B:
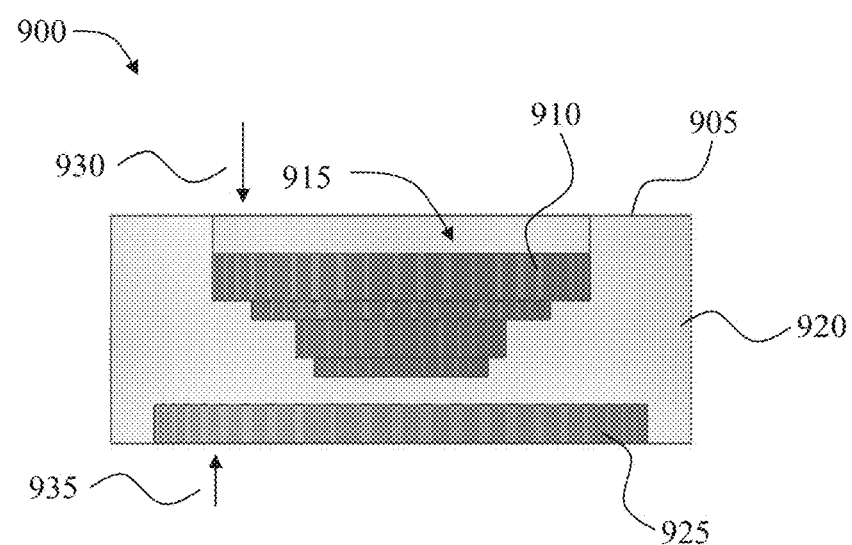

FIG. 9A shows an exemplary drug dosage form 900 formulated and configured to provide a desired drug release profile comprising a multi-layered structure comprising a plurality of layers of a first erodible material admixed with a drug 910, wherein the first erodible material is embedded in a second material not admixed with the drug 920 (pictured as a translucent material to allow for visualization of other components). The drug dosage form further comprises a layer of a third erodible material admixed with another drug 925, wherein the layer of the third erodible material admixed with the other drug is embedded in the second material not admixed with the drug (FIG. 9A). The drug dosage form 900 comprises a rim formed from the second material not admixed with the drug 905, wherein the rim forms a space 915 on top of the multi-layered structure (FIG. 9A). A cross-sectional view of the drug dosage form 900 is illustrated in FIG. 9B. The direction of erosion of the first erodible material admixed with the drug 910 is indicated by an arrow 930, and the direction of erosion of the third erodible material admixed with another drug 925 is indicated by an arrow 935 (FIG. 9B).

Additional Exemplary Embodiments

Embodiment 1

A method for three-dimensional printing of a drug dosage form formulated and configured to provide a desired drug release profile, comprising: dispensing a first erodible material admixed with a drug and a second material not admixed with the drug to produce a multi-layered structure comprising a plurality of layers of the first erodible material, wherein the first erodible material is embedded in the second material, wherein each layer of the first erodible material has a pre-determined surface area, thickness, and drug mass fraction, wherein the pre-determined surface area, thickness, and/or drug mass fraction correlate with the desired drug release profile, and wherein upon exposure to a bodily fluid the drug is released in accordance with the desired drug release profile.

Embodiment 2

The method of embodiment 1, further comprising providing the desired drug release profile prior to the dispensing step.

Embodiment 3

The method of embodiments 1 or 2, further comprising creating a virtual image of the drug dosage form prior to the dispensing step.

Embodiment 4

The method of any one of embodiments 1-3, further comprising creating a computer model that contains the pre-determined parameters prior to the dispensing step.

Embodiment 5

The method of any one of embodiments 1-4, further comprising feeding the pre-determined parameters to the three-dimensional printer prior to the dispensing step.

Embodiment 6

The method of any one of embodiments 1-5, wherein the first erodible material admixed with the drug and the second material not admixed with the drug are dispensed separately.

Embodiment 7

The method of any one of embodiments 1-6, wherein the first erodible material admixed with the drug and the second material not admixed with the drug are dispensed sequentially.

Embodiment 8

The method of any one of embodiments 1-7, wherein the surface areas of the first erodible material in at least two of the layers are different from each other.

Embodiment 9

The method of any one of embodiments 1-8, wherein the thicknesses of each of the plurality of layers of the first erodible material are the same.

Embodiment 10

The method of any one of embodiments 1-8, wherein the thickness of at least two of the layers of the first erodible materials are different from each other.

Embodiment 11

The method of any one of embodiments 1-10, wherein the drug mass fraction in each of the plurality of layers of the first erodible material are the same.

Embodiment 12

The method of any one of embodiments 1-10, wherein the drug mass fractions in at least two of the layers of the first erodible materials are different from each other.

Embodiment 13

The method of any one of embodiments 1-12, wherein the second material is a second erodible material.

Embodiment 14

The method of embodiment 13, wherein the first erodible material and the second erodible material are different from each other.

Embodiment 15

The method of embodiment 13, wherein the first erodible material and the second erodible material are the same.

Embodiment 16

The method of any one of embodiments 1-12, the second material is an insulating material that is impermeable to bodily fluid, wherein the insulating material forms a barrier between the bodily fluid and at least a portion of the multi-layered structure.

Embodiment 17

The method of any one of embodiments 13-15, further comprising dispensing an insulating material that is impermeable to bodily fluid, wherein the insulating material forms a barrier between the bodily fluid and at least a portion of the multi-layered structure.

Embodiment 18

The method of any one of embodiments 1-17, wherein the first erodible material and the second material are dispensed by different printing heads.

Embodiment 19

The method of embodiment 17, wherein the first erodible material, the second material, and the insulating material are dispensed by different printing heads.

Embodiment 20

The method of any one of embodiments 1-19, wherein the three-dimensional printing is carried out by fused deposition modeling (FDM).

Embodiment 21

The method of embodiment 20, wherein the FDM is non-filament FDM.

Embodiment 22

The method of any one of embodiments 1-15, wherein the first erodible material and the second material have the same erosion rate.

Embodiment 23

The method of any one of embodiments 1-22, wherein the thickness of each layer is no more than about 0.2 mm.

Embodiment 24

The method of any one of embodiments 1-15 and 17-23, further comprising dispensing an intermediate material not admixed with the drug, wherein the intermediate material forms an intermediate layer between two or more layers of the first erodible material.

Embodiment 25

The method of embodiment 24, wherein the intermediate material is the same as the first erodible material or the second material.

Embodiment 26

The method of embodiment 16, further comprising dispensing an intermediate material not admixed with the drug, wherein the intermediate material forms an intermediate layer between two or more layers of the first erodible material.

Embodiment 27

The method of embodiment 26, wherein the intermediate material is the same as the first erodible material.

Embodiment 28

The method of any one of embodiments 1-27, wherein the drug is to be released at an increasing rate.

Embodiment 29

The method of any one of embodiments 1-27, wherein the drug is to be released at a decreasing rate.

Embodiment 30

The method of any one of embodiments 1-27, wherein the drug is to be released at an increasing rate followed by a decreasing rate, or vice versa.

Embodiment 31

The method of any one of embodiments 1-27, wherein the drug is to be released in an oscillating pattern.

Embodiment 32

The method of any one of embodiments 1-31, wherein the drug dosage form further comprises a second drug.

Embodiment 33

The method of embodiment 32, wherein the second drug is admixed with the first erodible material.

Embodiment 34

The method of any one of embodiments 1-33, further comprising dispensing a third erodible material admixed with a second drug, wherein the multi-layered structure further comprises a plurality of layers of the third erodible material, wherein the third material is embedded in the second material.

Embodiment 35

The method of embodiment 34, wherein each layer of the third erodible material has a pre-determined surface area, thickness, and drug mass fraction, wherein the pre-determined surface area, thickness, and/or drug mass fraction correlate with a second desired drug release profile, and wherein upon exposure to the bodily fluid the second drug is released in accordance with the second desired drug release profile.

Embodiment 36

The method of embodiment 34 or 35, wherein the third erodible material is the same as the first erodible material.

Embodiment 37

The method of any one of embodiments 1-36, wherein the erosion of the first erodible material is pH dependent.

Embodiment 38

The method of any one of embodiments 34-37, wherein the erosion of the third erodible material is pH dependent.

Embodiment 39

The method of any one of embodiments 1-38, wherein the drug dosage form is an oral drug dosage form.

Embodiment 40

The method of any one of embodiments 1-39, wherein the bodily fluid is gastrointestinal fluid.

Embodiment 41

A method of designing a drug dosage form to provide a desired drug release profile, wherein the drug dosage form comprises a multi-layered structure comprising a plurality of layers of a first erodible material admixed with a drug, wherein the first erodible material is embedded in a second material not admixed with the drug, the method comprising:

(a) selecting the first erodible material and the second material for forming the multi-layered structure; (b) obtaining an erosion rate of first erodible material; and (c) determining the thickness, surface area, and/or drug mass fraction in each layer based on the release rate of the drug and the desired drug release profile.

Embodiment 42

The method of embodiment 41, further comprising obtaining the desired drug release profile.

Embodiment 43

The method of embodiment 41 or 42, further comprising dispensing the first erodible material admixed with the drug and the second material not admixed with the drug based on the determined thickness, surface area, and/or drug mass fraction.

Embodiment 44

The method of any one of embodiments 41-43, wherein the multi-layered structure further comprises a plurality of second layers of a third erodible material admixed with a second drug, and wherein the method further comprises: determining the drug release rate of the second drug from the third erodible material; and determining the thickness, surface area, and/or drug mass fraction in each second layer based on the release rate of the second drug and the desired drug release profile.

Embodiment 45

The method of embodiment 44, further comprising dispensing the third erodible material admixed with the second drug based on the determined thickness, surface area, and/or drug mass fraction.

Embodiment 46

A method for three-dimensional printing of a drug dosage form formulated and configured to provide a desired drug release profile, wherein the drug dosage form comprises a multi-layered structure comprising a plurality of layers of a first erodible material admixed with a drug, wherein the first erodible material is embedded in a second material not admixed with the drug, the method comprising: (a) determining the thickness, surface area, and/or drug mass fraction in each layer based on the release rate of the drug and the desired drug release profile; and (b) dispensing the first erodible material admixed with the drug and the second material not admixed with the drug based on the determined thickness, surface area, and/or drug mass fraction.

Embodiment 47

The method of any one of embodiments 41-46, wherein thickness (H) of the layer of the first erodible material is determined based on the erosion rate of the first erodible material admixed with the drug ($v_E$) and the time interval between two different datapoints on the drug release profile ($t_E$), wherein $H = t_E * v_E$.

Embodiment 48

The method of embodiment 47, wherein the drug mass fraction ($m_F$) in the first erodible material is determined based on the percentage, in decimal form, of the total drug in the drug dosage form that is in the layer of the erodible material admixed with the drug (% L), the total mass of the drug in the drug dosage form ($m_{DTot}$), the density of the erodible material admixed with the drug ($\rho$), and the volume ($V_{vol}$) of the layer of the erodible material, wherein $$m_F = \frac{\%_L * m_{DTot}}{\rho * V_{vol}}$$

Embodiment 49

The method of embodiment 48, wherein the total surface area ($S_t$) of the layers of the first erodible material that are exposed to the bodily fluid at the same time is determined by the drug mass fraction ($m_F$) and the thickness of the layers of first erodible material, wherein $$S_t = \frac{\%_L * m_{DTot}}{\rho * H * m_F}$$

Embodiment 50

The method of any one of embodiments 1-40 and 46-49, wherein the method further comprises: i) determining the drug release profile of the produced drug dosage form; ii) comparing the drug release profile of the drug dosage form with the desired drug release profile; and iii) adjusting the design of the drug dosage form by altering one or more of: the first erodible material, the second material, the surface area of the one or more of the layers of the first erodible material, the thickness of one or more layers of the first erodible material, and the mass fraction of the drug in one or more layers of the first erodible material.

Embodiment 51

A drug dosage form produced according to any one of the methods of embodiments 1-50.

Embodiment 52

The drug dosage form of claim 51, wherein the drug dosage form further comprises an enteric coating.

Embodiment 1'

A method for three-dimensional printing of an oral drug dosage form formulated and configured to provide a desired drug release profile, wherein the drug dosage form comprises a multi-layered structure comprising a plurality of layers of a first erodible material admixed with a drug, wherein the first erodible material is embedded in a second material not admixed with the drug, and wherein the second material is an insulating material that is impermeable to bodily fluid, and wherein the insulating material forms a barrier between the bodily fluid and at least a portion of the multi-layered structure, the method comprising: (a) providing a thickness and drug mass fraction in each layer; (b) determining the surface area of each layer based on the release rate of the drug and the desired drug release profile; and (b) dispensing the first erodible material admixed with the drug based on the provided thickness and drug mass faction and determined thickness; and (c) before, after, or during step (b), dispensing the second material not admixed with the drug.

Embodiment 2'

The method of embodiment 1', wherein the surface area on each layer of the first erodible material in the multi-layered structure is continuous.

Embodiment 3'

The method of embodiment 1', wherein the surface area on each layer of the first erodible material in the multi-layered structure is discontinuous.

Embodiment 4'

The method of embodiment 1', wherein the method further comprises dividing the desired drug release profile into time intervals ($t_E$) between two different data points on the drug release profile based on the number of layers of the first erodible material in the dosage form.

Embodiment 5'

The method of embodiment 4', wherein the thickness (H) of the layer of the first erodible material is based on the erosion rate of the first erodible material admixed with the drug ($v_E$) and the time interval ($t_E$) based on: $H=t_E*v_E$ Embodiment 6'

The method of embodiment 5', wherein the drug mass fraction ($m_F$) in the first erodible material is determined based on the percentage of a total drug in the drug dosage form that is in the layer of the erodible material admixed with the drug (% L), a total mass of the drug in the drug dosage form ($m_{DTot}$), a density of the erodible material admixed with the drug ($\rho$), and a volume ($V_{vol}$) of the layer of the erodible material, wherein $$m_F = \frac{\%_L * m_{DTot}}{\rho * V_{vol}}$$

Embodiment 7'

The method of embodiment 6', wherein the total surface area ($S_t$) of the layers of the first erodible material that are exposed to the bodily fluid at the same time is determined by a drug mass fraction ($m_F$) and the thickness of the layers of first erodible material, wherein $$S_t = \frac{\%_L * m_{DTot}}{\rho * H * m_F}$$

Embodiment 8'

The method of any one of embodiments 1'-7', further comprising: i) determining the drug release profile of the produced drug dosage form; ii) comparing the drug release profile of the drug dosage form with the desired drug release profile; and iii) adjusting the design of the drug dosage form by altering one or more of: the first erodible material, the second material, the surface area of the one or more of the layers of the first erodible material, the thickness of one or more layers of the first erodible material, and the mass fraction of the drug in one or more layers of the first erodible material.

Embodiment 9'

The method of any one of embodiments 1'-8', further comprising: dispensing a third erodible material admixed with a second drug and the second material not admixed with the second drug to produce a structure of the third erodible material, wherein the third erodible material is embedded in the second material, and wherein upon exposure to a bodily fluid the second drug is released in accordance with a second desired drug release profile.

Embodiment 10'

The method of any one of embodiments 1'-9', further comprising: selecting the first erodible material and the second material for forming the multi-layered structure and obtaining an erosion rate of the first erodible material prior to determining the thickness, surface area, and drug mass fraction in each layer.

Embodiment 11'

The method of any one of embodiments 1'-10', further comprising providing the desired drug release profile prior to the determining step.

Embodiment 12'

The method of any one of embodiments 1'-11', further comprising creating a virtual image of the drug dosage form based on the determined parameters prior to the dispensing step.

Embodiment 13'

The method of any one of embodiments 1'-12', wherein the first erodible material admixed with the drug and the second material not admixed with the drug are dispensed separately.

Embodiment 14'

The method of any one of embodiments 1'-13', wherein the thickness of each layer is no more than about 0.2 mm.

Embodiment 15'

The method of any one of embodiments 1'-14', wherein the surface area of each of the plurality of the layers of the first erodible material in the multi-layered structure decreases sequentially from the surface to the interior of the oral dosage form, wherein when the oral dosage form is exposed to a bodily fluid the plurality of layers are exposed to the bodily fluid in a sequential pattern, with the layer with the largest surface area exposed to the bodily fluid first.

Embodiment 16'

The method of any one of embodiments 1'-15', wherein the three-dimensional printing is carried out by fused deposition modeling (FDM).

Embodiment 17'

The method of embodiment 16', wherein the FDM is non-filament FDM.

Embodiment 18'

The method of any one of embodiments 1'-17', wherein the desired release profile is a pulsed release profile.

Embodiment 19'

The method of any one of embodiments 1'-17', wherein the drug is to be released in a first order release profile.

Embodiment 20'

An oral dosage form produced by the method of any one of embodiments 1'-19'.

Embodiment 21'

A method or designing an oral drug dosage form to provide a desired drug release profile, wherein the drug dosage form comprises a multi-layered structure comprising a plurality of layers of a first erodible material admixed with a drug, wherein the first erodible material is embedded in a second material not admixed with the drug, the method comprising: (a) selecting the first erodible material and the second material for forming the oral dosage form comprising the multi-layered structure; (b) obtaining an erosion rate of first erodible material; and (c) determining the thickness, surface area, and drug mass fraction in each layer based on the release rate of the drug and the desired drug release profile.

Embodiment 22'

The method of embodiment 24, further comprising dispensing the first erodible material admixed with the drug and the second material not admixed with the drug based on the determined thickness, surface area, and drug mass fraction.

Embodiment 1"

A method for three-dimensional printing of an oral drug dosage form formulated and configured to provide a desired drug release profile, wherein the drug dosage form comprises a multi-layered structure comprising a plurality of layers of a first erodible material admixed with a drug, wherein the first erodible material is embedded in a second material not admixed with the drug, the method comprising: (a) determining the thickness, surface area, and drug mass fraction in each layer based on the release rate of the drug and the desired drug release profile; and (b) dispensing the first erodible material admixed with the drug based on the determined thickness, surface area, and drug mass fraction; and (c) before, after, or during step (b), dispensing the second material not admixed with the drug.

Embodiment 2"

The method of embodiment 1, wherein the second material is a second erodible material.

Embodiment 3"

The method of embodiment 1, wherein the second material is an insulating material that is impermeable to bodily fluid, and wherein the insulating material forms a barrier between the bodily fluid and at least a portion of the multi-layered structure.

Embodiment 4"

The method of any one of embodiments 1"-3", wherein the thickness and drug fraction of each layer of the first erodible material in the multi-layered structure are constant and the surface area of in each layer correlates with the desired drug release profile.

Embodiment 5"

The method of embodiment 4", wherein the surface areas of the first erodible material in at least two of the layers are different from each other.

Embodiment 6"

The method of any one of the embodiments 1"-5", wherein the surface area of each layer of the first erodible material in the multi-layered structure is continuous.

Embodiment 6"

The method of any one of embodiments 1"-5", wherein the surface area of each layer of the first erodible material in the multi-layered structure is discontinuous.

Embodiment 7"

The method of any one of embodiments 1-6, wherein the method further comprises dividing the desired drug release profile into time intervals ($t_E$) between two different data points on the drug release profile based on the number of layers of the first erodible material in the dosage form.

Embodiment 8"

The method of embodiment 7", wherein the thickness (H) of the layer of the first erodible material is based on the erosion rate of the first erodible material admixed with the drug ($v_E$) and the time interval ($t_E$) based on: $H=t_E*v_E$ Embodiment 9"

The method of embodiment 8, wherein the drug mass fraction ($m_F$) in the first erodible material is determined based on the percentage, in decimal form, of a total drug in the drug dosage form that is in the layer of the erodible material admixed with the drug (% L), a total mass of the drug in the drug dosage form ($m_{DTot}$), a density of the erodible material admixed with the drug ($\varphi$, and a volume ($V_{vol}$) of the layer of the erodible material, wherein $$m_F = \frac{\%_L * m_{DTot}}{\rho * V_{vol}}$$

Embodiment 10"

The method of embodiment 9", wherein the total surface area ($S_t$) of the layers of the first erodible material that are exposed to the bodily fluid at the same time is determined by a drug mass fraction ($m_F$) and the thickness of the layers of first erodible material, wherein $$S_t = \frac{\%_L * m_{DTot}}{\rho * H * m_F}$$

Embodiment 11"

The method of any one of embodiments 1"-10", further comprising: i) determining the drug release profile of the produced drug dosage form; ii) comparing the drug release profile of the drug dosage form with the desired drug release profile; and iii) adjusting the design of the drug dosage form by altering one or more of: the first erodible material, the second material, the surface area of the one or more of the layers of the first erodible material, the thickness of one or more layers of the first erodible material, and the mass fraction of the drug in one or more layers of the first erodible material.

Embodiment 12"

The method of any one of embodiments 1"-11", further comprising: dispensing a third erodible material admixed with a second drug and the second material not admixed with the second drug to produce a structure of the third erodible material, wherein the third erodible material is embedded in the second material, wherein upon exposure to a bodily fluid the second drug is released in accordance with a second desired drug release profile.

Embodiment 13"

The method of any one of embodiments 1"-12", further comprising: selecting the first erodible material and the second material for forming the multi-layered structure and obtaining an erosion rate of the first erodible material prior to determining the thickness, surface area, and drug mass fraction in each layer.

Embodiment 14"

The method of any one of embodiments 1"-13", further comprising providing the desired drug release profile prior to the determining step.

Embodiment 15"

The method of any one of embodiments 1"-14", further comprising creating a virtual image of the drug dosage form based on the determined parameters prior to the dispending step.

Embodiment 16"

The method of any one of embodiments 1"-15", wherein the first erodible material admixed with the drug and the second material not admixed with the drug are dispensed separately.

Embodiment 17"

The method of any one of embodiments 1"-16", wherein the thickness of each layer is no more than about 0.2 mm.

Embodiment 18"

The method of any one of embodiments 1"-17", wherein the surface area of each of the plurality of the layers of the first erodible material in the multi-layered structure decreases sequentially from the surface to the interior of the oral dosage form, wherein when the oral dosage form is exposed to a bodily fluid the plurality of layers are exposed to the bodily fluid in a sequential pattern, with the layer with the largest surface area exposed to the bodily fluid first.

Embodiment 19"

The method of any one of embodiments 1"-18", wherein the three-dimensional printing is carried out by fused deposition modeling (FDM).

Embodiment 20"

The method of embodiment 19", wherein the FDM is non-filament FDM.

Embodiment 21"

The method of any one of embodiments 1"-20", wherein the desired release profile is a pulsed release profile.

Embodiment 22"

The method of any one of embodiments 1"-20", wherein the drug is to be released in a first order release profile.

Embodiment 23"

An oral dosage form produced by the method of any one of embodiments 1"-23".

Embodiment 24"

A method or designing an oral drug dosage form to provide a desired drug release profile, wherein the drug dosage form comprises a multi-layered structure comprising a plurality of layers of a first erodible material admixed with a drug, wherein the first erodible material is embedded in a second material not admixed with the drug, the method comprising: (a) selecting the first erodible material and the second material for forming the oral dosage form comprising the multi-layered structure; (b) obtaining an erosion rate of first erodible material; and (c) determining the thickness, surface area, and drug mass fraction in each layer based on the release rate of the drug and the desired drug release profile.

Embodiment 25"

The method of embodiment 24", further comprising dispensing the first erodible material admixed with the drug and the second material not admixed with the drug based on the determined thickness, surface area, and drug mass fraction.

Embodiment 1'''

A method for three-dimensional printing of an oral drug dosage form formulated and configured to provide a desired drug release profile, wherein the drug dosage form comprises a multi-layered structure comprising a plurality of layers of a first erodible material admixed with a drug having a pre-determined drug mass faction ($m_F$), wherein the first erodible material is embedded in a second material not admixed with the drug, the method comprising: (a) dividing the desired drug release profile into a plurality of time intervals ($t_n$), each time interval corresponding to a layer in the multi-layered structure; (b) calculating the percentage of drugs to be released during each time interval ($\%_L$); (c) calculating the thickness of each layer ($H_n$) of the multi-layered structure based on the erosion rate of the first erodible material (V), wherein $H_n = t_n*V$; (d) calculating the surface area of each layer based on $\%_L$, $H_n$, $m_F$, total amount of drug in the oral drug dosage form ($m_{DTot}$), and the density of the first erodible material ($\rho$), wherein:

$$S_n = \frac{\%_L * m_{DTot}}{\rho * Hn * m_F}$$

(e) dispensing the first erodible material admixed with the drug based on the determined $H_n$ and $S_n$ for each layer, thereby printing the multi-layered structure; (f) before, after, or during step (e), dispensing the second material not admixed with the drug.

Embodiments 2'''

The method of embodiment 1''', further comprising dispensing a top erodible material not admixed with the drug on top of the multi-layered structure to form a top layer, wherein the surface area of the top layer is the same or larger than the first layer of the multi-layered structure immediately underneath the top layer.

Embodiment 3'''

The method of embodiment 2''', wherein the thickness of the top layer is determined based on the delay time needed for the drug release from the multi-layered structure.

Embodiment 4'''

The method of embodiment 2''' or 3''', wherein the top erodible material is the same as the first erodible material.

Embodiment 5'''

The method of embodiment 2''' or 3''', wherein the top erodible material is different from the first erodible material.

Embodiment 6'''

The method of any one of embodiments 1'''-5''', wherein the second material is erodible.

Embodiment 7'''

The method of embodiment 6''', wherein the first erodible material and the second material have the same erosion rate.

Embodiment 8'''

The method of any one of embodiments 1'''-5''', wherein the second material is an insulating material that is impermeable to bodily fluid, wherein the insulating material forms a barrier between the bodily fluid and at least a portion of the multi-layered structure.

Embodiment 9'''

The method of any one of embodiments 1'''-8''', further comprising dispensing an insulating material that is impermeable to bodily fluid, wherein the insulating material forms a barrier between the bodily fluid and at least a portion of the multi-layered structure.

Embodiment 10'''

The method of any embodiments 1'''-9''', further comprising dispensing an intermediate material not admixed with the drug, wherein the intermediate material forms one or more intermediate layers between two or more layers of the first erodible material.

Embodiment 11'''

The method of embodiment 10''', wherein the intermediate material is the same as the first erodible material.

Embodiment 12'''

The method of embodiment 10''', wherein the intermediate layer is different from the first erodible material.

Embodiment 13'''

The method of any one of embodiments 1'''-12''', wherein the three-dimensional printing is carried out by fused deposition modeling (FDM).

Embodiment 14'''

The method of embodiment 14''', wherein the FDM is non-filament FDM.

Embodiment 15'''

The method of any one of embodiments 1'''-14''', wherein the first erodible material and the second material are printed by different printing heads.

Embodiment 16'''

The method of any one of embodiments 2'''-15''', wherein the first erodible material and the top erodible material are printed by different printing heads.

Embodiment 17'''

The method of any one of embodiments 9'''-16''', wherein the first erodible material, the second erodible material, and the insulating material are printed by a different printing heads.

Embodiment 18'''

The method of any one of embodiments 1'''-17''', further comprising: i) determining the drug release profile of the oral drug dosage form produced by the method of any one of embodiments 1-17; ii) comparing the drug release profile of the oral drug dosage form with the desired drug release profile; iii) adjusting one or more parameters selected from: the first erodible material, the second material, the surface area of the one or more of the layers of the first erodible material, the thickness of one or more layers of the first erodible material, and the mass fraction of the drug in one or more layers of the first erodible material; and iv) three-dimensional printing of a second oral drug dosage form based on the adjusted parameters.

Embodiment 19'''

The method of any one of embodiments 1'''-18''', wherein the release profile of the oral drug dosage form or second drug oral dosage form is equivalent to the desired release profile based on Chow's method or similarity factor calculation method.

Embodiment 20'''

The method of any one of embodiments 1'''-19''', further comprising creating a virtual image of the drug dosage form prior to the dispending steps.

Embodiment 21'''

The method of any one of embodiments 1'''-20''', further comprising creating a computer model that contains the pre-determined parameters prior to the dispensing step.

Embodiment 22'''

The method of any one of embodiments 1'''-21''', further comprising feeding the pre-determined parameters to the three-dimensional printer prior to the dispensing step.

Embodiment 23'''

The method of any one of embodiments 1'''-22''', wherein the surface area of each of the plurality of the layers of the first erodible material in the multi-layered structure decreases sequentially from the surface to the interior of the oral dosage form, wherein when the oral dosage form is exposed to a bodily fluid the plurality of layers are exposed to the bodily fluid in a sequential pattern, with the layer with the largest surface area exposed to the bodily fluid first.

Embodiment 24'''

The method of any one of embodiments 1'''-23''', wherein the oral drug dosage form comprises two or more multi-layered structures.

Embodiment 25'''

A method for three-dimensional printing of an oral drug dosage form formulated and configured to provide a first desired drug release profile and a second desired drug release profile, wherein the drug dosage form comprises a first multi-layered structure comprising a plurality of layers of a first erodible material admixed with a drug having a pre-determined drug mass faction ($m_F$), wherein the first erodible material is embedded in a second material not admixed with a first drug, and a second multi-layered structure comprising a plurality of layers of a third erodible material admixed with a fourth drug having a pre-determined drug mass faction, wherein the third erodible material is embedded in a fourth material not admixed with the drug, the method comprising: (a) dividing each of the desired drug release profile into a plurality of time intervals ($t_n$), each time interval corresponding to a layer in a corresponding multi-layered structure; (b) calculating the percentage of drugs to be released during each time interval ($\%_L$); (c) calculating the thickness of each layer ($H_n$) of the multi-layered structures based on the erosion rate of the first erodible material or third erodible material (V), wherein $H_n=t_n*V$; (d) calculating the surface area of each layer based on $\%_L$, $H_n$, $m_F$, total amount of drug in the oral drug dosage form ($m_{DTot}$), and the density of the first or first erodible material ($\rho$), wherein:

$$S_n = \frac{\%_L * m_{DTot}}{\rho * Hn * m_F}$$

(e) dispensing the first erodible material admixed with the first drug and third erodible material admixed with the second drug based on the determined $H_n$ and $S_n$ for each layer, thereby printing the two multi-layered structures; and (f) before, after, or during step (e), dispensing the second material and fourth material not admixed with the drug.

Embodiment 26'''

The method of embodiment 25''', wherein the first erodible material and the third erodible material are the same.

Embodiment 27'''

The method of embodiment 25''' or 26''', wherein the second and fourth materials are the same.

Embodiment 28'''

The method of any one of embodiments 25'''-27''', wherein the first drug and the second drug are the same.

Embodiment 29'''

The method of any one of embodiments 25-28, wherein the first drug and the second drug are different.

Embodiment 30'''

An oral dosage form produced by the method of any one of embodiments 1'''-29'''.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects. Rather, the scope of this disclosure should be determined with reference to the appended claims.

The disclosure is illustrated further by the following examples, which are not to be construed as limiting the disclosure in scope or spirit to the specific procedures described in them.

EXAMPLES

Example 1

Designing an Oral Drug Dosage Form to Provide Desired Drug Release Profiles

This example demonstrates designing an oral drug dosage form comprising an ADHD non-stimulant (clonidine, 0.1 mg) and an ADHD stimulant (dextromethylphenidate, 2.5 mg), wherein the ADHD non-stimulant has a sustained release profile and the ADHD stimulant has a fast release profile.

Figure 10:
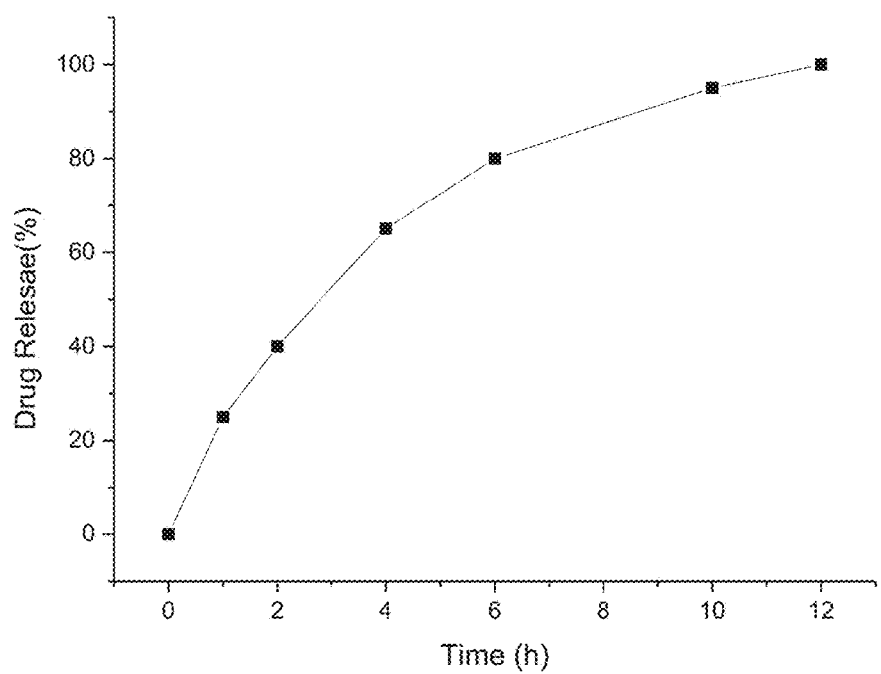
FIG. 10 shows a graph of a desired drug release profile (drug release (%) versus time (hour)).

The desired drug release profile was selected for the sustained release profile of clonidine (see FIG. 10). The desired drug release profile of the ADHD non-stimulant was segmented into six time sections. The time after administration (hours) was then tabulated with the cumulative percentage of clonidine released from the drug dosage form after administration (Table 1).

TABLE 1

Cumulative percentage of clonidine release after administration.

| Time after administration (hours) | Cumulative percentage of clonidine released (%) |
| --- | --- |
| 1 | 25 |
| 2 | 40 |
| 4 | 65 |
| 6 | 80 |
| 10 | 95 |
| 12 | 100 |

Using this information, the percentage of total clonidine released form the drug dosage form was tabulated per time section (Table 2). As shown in Table 2, each time section corresponds to a layer of the multi-layered structure of the drug dosage form.

TABLE 2

Percentage of total clonidine released per layer.

| Layer No. | Erosion time (hour) | Percentage of total clonidine released (%) |
| --- | --- | --- |
| 1 | 1 | 25 |
| 2 | 1 | 15 |
| 3 | 2 | 25 |
| 4 | 2 | 15 |
| 5 | 4 | 15 |
| 6 | 2 | 5 |

Using the information from Table 2, a hypothetical erosion rate of the erodible material for the layers of the multi-layered structure was calculated using hypothetical ranges of layer thicknesses that were appropriate for a 3D printed oral drug dosage form (e.g., an oral dosage form that may be printed, e.g., minimum overall dimensions greater than 2 mm, but was not too large for oral administration, e.g., less than 25 mm).

From a database of possible erodible materials that would provide the desired erosion rate, hydroxyl propyl cellulose (HPC) admixed with triethyl citrate (TEC) (weight ratio of HPC:TEC of 79.68:19.92) was selected as the erodible material for the multi-layered structure (erosion rate of 0.13 mm/hour). The erosion rate of HPC admixed with TEC was confirmed not to change when the material was admixed with an appropriate range of amounts of clonidine. Using the erosion rate of HPC admixed with TEC and the information in Table 2, the thickness of each of the six layers of the multi-layered structure was calculated using Formula III. The thickness of each of the six layers is listed in Table 3.

TABLE 3

Thickness of each layer.

| Layer No. | Erosion time (hour) | Layer thickness (mm) |
| --- | --- | --- |
| 1 | 1 | 0.13 |
| 2 | 1 | 0.13 |
| 3 | 2 | 0.26 |
| 4 | 2 | 0.26 |
| 5 | 4 | 0.52 |
| 6 | 2 | 0.26 |

Next, the surface area and amount of drug compound (e.g., drug) mass fraction, of each layer of the multi-layered structure were calculated using Formula V. A single drug mass fraction of the HPC:TEC admixed with clonidine was selected to allow for use of one printer head containing the erodible material comprising clonidine for production of the oral drug dosage form. Using this information, the layers of the multi-layered structure were selected to be cylindrical in shape and the multi-layered structure was drawn for 3D printing conforming to the surface area and thickness calculated for each layer.

The fast release profile, e.g., instant or immediate release, of the ADHD stimulant dextromethylphenidate was selected to provide release at least 80% of the total dextromethylphenidate within 15 minutes of oral administration. Vinylpyrrolidone-vinyl acetate copolymer (VA64) admixed with TEC (weight ratio of VA64:TEC of 79.2:8.10) was selected as the erodible material for admixture with dextromethylphenidate (2.5 mg). The total weight of the VA64:TEC:dextromethylphenidate material was measured as 25 mg. Then the density and volume of the VA64:TEC:dextromethylphenidate material were determined. Using this information, the VA64:TEC:dextromethylphenidate material structure was drawn for 3D printing (cylindrical structure with a 0.52 mm thickness and a diameter of 6.8 mm).

Using the parameters of the multi-layered structure comprising clonidine and the single-layered disc comprising dextromethylphenidate, an oral drug dosage form was compiled by embedding the structures in an insulating material, namely, EUDRAGIT® RSPO (RSPO), wherein the multi-layered structure and the single-layered disc were separated with insulating material (such as shown in FIG. 9B). The oral drug dosage form was printed using non-filament FDM (for initial printing and testing dextromethylphenidate was substituted with propranolol HCl).

The oral drug dosage form was tested using in vitro dissolution testing (similarity factor (f2) testing was used for statistical analysis). It was determined that the top layer (layer no. 1) of the multi-layered structure eroded at a faster rate than expected. In order to improve the clonidine release profile of the oral drug dosage form, the top three layers (layer nos. 1-3; Table 2) were merged into a single layer with parameters that would meet the desired drug release profile. Furthermore, the surface area of the original top layer was adjusted to reduce the surface area as compared to the original layer. The adjusted oral drug dosage form was printed using non-filament FDM (for initial printing and testing dextromethylphenidate was substituted with propranolol HCl) and in vitro dissolution testing was performed to demonstrate compliance with the desired drug release profiles. The in vitro dissolution release profile of the adjusted printed oral drug dosage form demonstrated statistical similarity using similarity factor (f2) statistical analysis.

What is claimed is:

1. A method for three-dimensional printing of an oral drug dosage form formulated and configured to provide a desired drug release profile, wherein the drug dosage form comprises a multi-layered structure comprising a plurality of layers of a first erodible material admixed with a drug having a pre-determined drug mass faction ($m_F$), wherein the first erodible material is embedded in a second material not admixed with the drug, the method comprising:
    (a) dividing the desired drug release profile into a plurality of time intervals ($t_n$), each time interval corresponding to a layer in the multi-layered structure;
    (b) calculating the percentage of drugs to be released during each time interval ($\%_L$);
    (c) calculating the thickness of each layer ($H_n$) of the multi-layered structure based on the erosion rate of the first erodible material (V), wherein $H_n = t_n * V$;
    (d) calculating the surface area of each layer based on $\%_L$, $H_n$, $m_F$, total amount of drug in the oral drug dosage form ($m_{DTot}$), and the density of the first erodible material ($\rho$), wherein:

$$S_n = \frac{\%_L * m_{DTot}}{\rho * Hn * m_F};$$

(e) dispensing the first erodible material admixed with the drug based on the determined $H_n$ and $S_n$ for each layer, thereby printing the multi-layered structure;
    (f) before, after, or during step (e), dispensing the second material not admixed with the drug.

2. The method of claim 1, further comprising dispensing a top erodible material not admixed with the drug on top of the multi-layered structure to form a top layer, wherein the surface area of the top layer is the same or larger than the first layer of the multi-layered structure immediately underneath the top layer.

3. The method of claim 2, wherein the thickness of the top layer is determined based on the delay time needed for the drug release from the multi-layered structure.

4. The method of claim 2, wherein the top erodible material is the same as the first erodible material.

5. The method of claim 2, wherein the top erodible material is different from the first erodible material.

6. The method of claim 1, wherein the second material is erodible.

7. The method of claim 6, wherein the first erodible material and the second material have the same erosion rate.

8. The method of claim 1, wherein the second material is an insulating material that is impermeable to bodily fluid, wherein the insulating material forms a barrier between the bodily fluid and at least a portion of the multi-layered structure.

9. The method of claim 1, further comprising dispensing an insulating material that is impermeable to bodily fluid, wherein the insulating material forms a barrier between the bodily fluid and at least a portion of the multi-layered structure.

10. The method of claim 1, further comprising dispensing an intermediate material not admixed with the drug, wherein the intermediate material forms one or more intermediate layers between two or more layers of the first erodible material.

11. The method of claim 10, wherein the intermediate material is the same as the first erodible material.

12. The method of claim 10, wherein the intermediate layer is different from the first erodible material.

13. The method of claim 1, wherein the three-dimensional printing is carried out by fused deposition modeling (FDM).

14. The method of claim 13, wherein the FDM is non-filament FDM.

15. The method of claim 1, wherein the first erodible material and the second material are printed by different printing heads.

16. The method of claim 1, wherein the first erodible material and the top erodible material are printed by different printing heads.

17. The method of claim 1, wherein the first erodible material, the second erodible material, and the insulating material are printed by a different printing heads.

18. The method of claim 1, further comprising:
    i) determining the drug release profile of the oral drug dosage form produced by the method of claim 1;
    ii) comparing the drug release profile of the oral drug dosage form with the desired drug release profile;
    iii) adjusting one or more parameters selected from: the first erodible material, the second material, the surface area of the one or more of the layers of the first erodible material, the thickness of one or more layers of the first erodible material, and the mass fraction of the drug in one or more layers of the first erodible material; and
    iv) three-dimensional printing of a second oral drug dosage form based on the adjusted parameters.

19. The method of claim 1, wherein the release profile of the oral drug dosage form or second drug oral dosage form is equivalent to the desired release profile based on Chow's method or similarity factor calculation method.

20. The method of claim 1, further comprising creating a virtual image of the drug dosage form prior to the dispending steps.

21. The method of claim 1, further comprising creating a computer model that contains the pre-determined parameters prior to the dispensing step.

22. The method of claim 1, further comprising feeding the pre-determined parameters to the three-dimensional printer prior to the dispensing step.

23. The method of claim 1, wherein the surface area of each of the plurality of the layers of the first erodible material in the multi-layered structure decreases sequentially from the surface to the interior of the oral dosage form, wherein when the oral dosage form is exposed to a bodily fluid the plurality of layers are exposed to the bodily fluid in a sequential pattern, with the layer with the largest surface area exposed to the bodily fluid first.

24. The method of claim 1, wherein the oral drug dosage form comprises two or more multi-layered structures.

25. A method for three-dimensional printing of an oral drug dosage form formulated and configured to provide a first desired drug release profile and a second desired drug release profile, wherein the drug dosage form comprises a first multi-layered structure comprising a plurality of layers of a first erodible material admixed with a drug having a pre-determined drug mass faction ($m_F$), wherein the first erodible material is embedded in a second material not admixed with a first drug, and a second multi-layered structure comprising a plurality of layers of a third erodible material admixed with a fourth drug having a pre-determined drug mass faction, wherein the third erodible material is embedded in a fourth material not admixed with the drug, the method comprising:

(a) dividing each of the desired drug release profile into a plurality of time intervals ($t_n$), each time interval corresponding to a layer in a corresponding multi-layered structure;

(b) calculating the percentage of drugs to be released during each time interval ($\%_L$);

(c) calculating the thickness of each layer ($H_n$) of the multi-layered structures based on the erosion rate of the first erodible material or third erodible material (V), wherein $H_1=t_n*V$;

(d) calculating the surface area of each layer based on $\%_L$, $H_n$, $m_F$, total amount of drug in the oral drug dosage form ($m_{DTot}$), and the density of the first or first erodible material ($\rho$), wherein:

$$S_n = \frac{\%_L * m_{DTot}}{\rho * Hn * m_F};$$

(e) dispensing the first erodible material admixed with the first drug and third erodible material admixed with the second drug based on the determined $H_n$ and $S_n$ for each layer, thereby printing the two multi-layered structures;

(f) before, after, or during step (e), dispensing the second material and fourth material not admixed with the drug.

26. The method of claim 25, wherein the first erodible material and the third erodible material are the same.

27. The method of claim 25, wherein the second and fourth materials are the same.

28. The method of claim 25, wherein the first drug and the second drug are the same.

29. The method of claim 25, wherein the first drug and the second drug are different.

* * * * *